US011883460B2

(12) United States Patent
Heng et al.

(10) Patent No.: US 11,883,460 B2
(45) Date of Patent: Jan. 30, 2024

(54) ANTIBIOTIC COMPOSITIONS FOR TREATING BACTERIAL INFECTIONS

(71) Applicants: AGENCY FOR SCIENCE, TECHNOLOGY AND RESEARCH, Singapore (SG); National University Hospital (Singapore) PTE LTD, Singapore (SG)

(72) Inventors: Desmond Heng, Singapore (SG); Sie Huey Lee, Singapore (SG); Jeanette Teo, Singapore (SG); Wai Kiong Ng, Singapore (SG); Reginald Tan, Singapore (SG)

(73) Assignees: Agency for Science, Technology and Research, Singapore (SG); National University Hospital (Singapore) PTE Ltd, Singapore (SG)

( * ) Notice: Subject to any disclaimer, the term of this patent is extended or adjusted under 35 U.S.C. 154(b) by 52 days.

(21) Appl. No.: 17/175,525

(22) Filed: Feb. 12, 2021

(65) Prior Publication Data

US 2021/0236589 A1 Aug. 5, 2021

Related U.S. Application Data

(62) Division of application No. 15/329,244, filed as application No. PCT/SG2015/050235 on Jul. 24, 2015, now Pat. No. 10,953,070.

(30) Foreign Application Priority Data

Jul. 25, 2014 (SG) .......................... 10201404407X

(51) Int. Cl.
| | |
|---|---|
| *A61K 38/12* | (2006.01) |
| *A61K 9/00* | (2006.01) |
| *A61K 31/496* | (2006.01) |
| *A61K 31/407* | (2006.01) |
| *A61K 31/65* | (2006.01) |
| *A61K 45/06* | (2006.01) |
| *A61K 9/16* | (2006.01) |

(52) U.S. Cl.
CPC ............ *A61K 38/12* (2013.01); *A61K 9/0075* (2013.01); *A61K 9/1688* (2013.01); *A61K 31/407* (2013.01); *A61K 31/496* (2013.01); *A61K 31/65* (2013.01); *A61K 45/06* (2013.01); *Y02A 50/30* (2018.01)

(58) Field of Classification Search
CPC .... A61K 38/12; A61K 9/0075; A61K 31/407; A61K 31/496; A61K 31/65
See application file for complete search history.

(56) References Cited

U.S. PATENT DOCUMENTS

| | | | |
|---|---|---|---|
| 2003/0053960 A1 | 3/2003 | Heijerman et al. | |
| 2005/0065141 A1 | 3/2005 | Odink et al. | |
| 2013/0202616 A1 | 8/2013 | Spellberg et al. | |
| 2015/0107589 A1 | 4/2015 | Longest et al. | |

FOREIGN PATENT DOCUMENTS

| | | |
|---|---|---|
| CN | 103110633 A | 5/2013 |
| WO | 2012061902 A1 | 5/2012 |
| WO | 2013011019 A1 | 1/2013 |
| WO | 2013104892 A1 | 7/2013 |

OTHER PUBLICATIONS

Ocampo et al., "Antagonism between Bacteriostatic and Bactericidal Antibiotics Is Prevalent", Antimicrobial Agents and Chemotherapy, Jul. 15, 2014, 10 pages, vol. 58, No. 8.
Ahmed et al., "Current concepts in combination antibiotic therapy for critically ill patients," Indian Journal of Critical Care Medicine, May 2014, 5 pages, vol. 18, No. 5.
Lu et al., "Efficacy of High-dose Nebulized Colistin in Ventilator-associated Pneumonia Caused by Multidrug-resistant Pseudomonas aeruginosa and Acinetobacter baumannii," Anesthesiology, Dec. 2012, 13 pages, vol. 117, No. 6, The American Society of Anesthestologists, Inc.
Malone et al., "Carbapenem-associated multidrug-resistant Acinetobacter baumannii are sensitised by aztreonam in combination with polyamines," International Journal of Antimicrobial Agents, Jan. 2013, 11 pages, vol. 41, No. 1.
The Written Opinion for Singaporean Application No. 11201700621X dated Feb. 14, 2019, 9 pages.
Zhou et al., "Synergistic Antibiotic Combination Powders of Colistin and Rifampicin Provide High Aerosolization Efficiency and Moisture Protection", The AAPS Journal, Oct. 16, 2013, 11 pages, vol. 16, No. 1.
Biancofiore et al., "Colistin, meropenem and rifampin in a combination therapy for multi-drug-resistant Acinetobacter baumannii multifocal infection", Minerva Anestesiologica, Mar. 2007, 5 pages, vol. 73, No. 3.
Heng et al., "Synergistic Combination Dry Powders for Inhaled Antimicrobial Therapy", Powders and Grains 2013, AIP Conference Proceedings 1542, 2013, 4 pages.
Zarogoulidis et al., "Clinical experimentation with aerosol antibiotics: current and future methods of administration", Drug Design, Development and Therapy, 2013, 20 pages, vol. 7.
Yoon et al., In Vitro Double and Triple Synergistic Activities of Polymyxin B, Imipenem, and Rifampin against Multidrug-Resistant Acinetobacter baumannil, Antimicrobial Agents and Chemotherapy, Nov. 12, 2003, 5 pages, vol. 48, No. 3.
PCT Notification of Transmittal of the International Search Report and the Written Opinion of the International Searching Authority, or the Declaration for PCT Counterpart Application No. PCT/SG2015/050235 dated Sep. 10, 2015, 14 pages.

(Continued)

*Primary Examiner* — Snigdha Maewall
(74) *Attorney, Agent, or Firm* — Womble Bond Dickinson (US) LLP

(57) ABSTRACT

The present disclosure provides dry powder antibiotic compositions that are effective in the treatment of bacterial infections and associated conditions. Moreover, the present disclosure provides dry powder antibiotic compositions for the treatment of bacterial infections, by multi-drug resistant bacteria, resulting in the subsequent reduction in the prevalent rates of drug resistance.

21 Claims, 9 Drawing Sheets

(56) References Cited

OTHER PUBLICATIONS

PCT Notification of Transmittal of International Preliminary Report on Patentability (Chapter II of the Patent Cooperation Treaty) for PCT Counterpart Application No. PCT/SG2015/050235 dated Nov. 15, 2016, 21 pages.

[Fig.1]
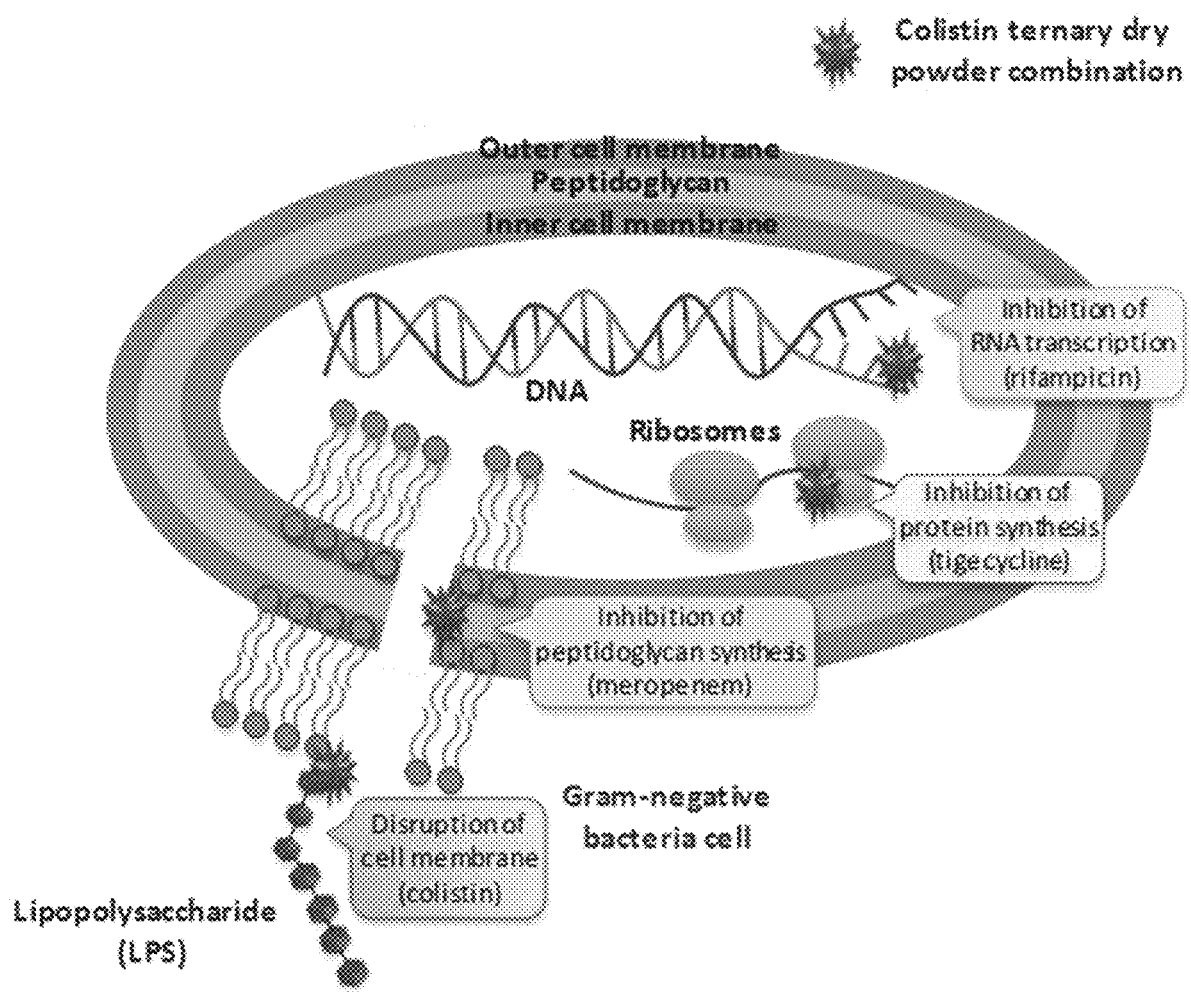

[Fig. 2]
a)
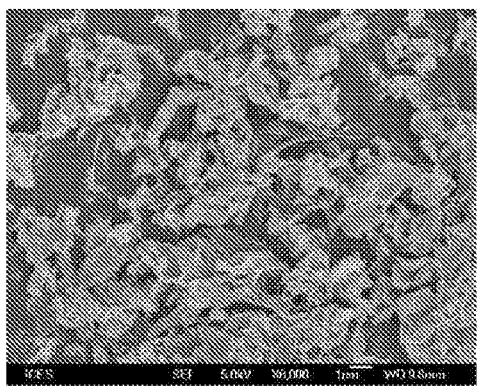
b)
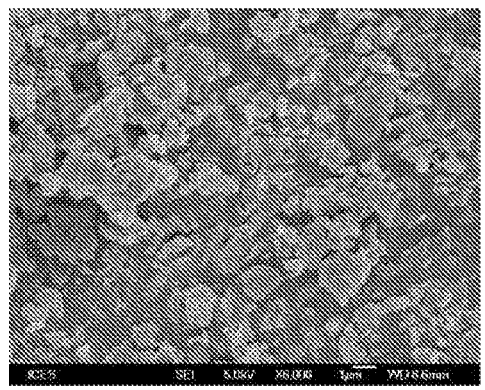
c)
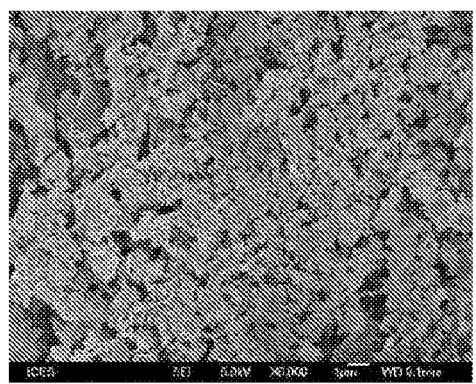
d)
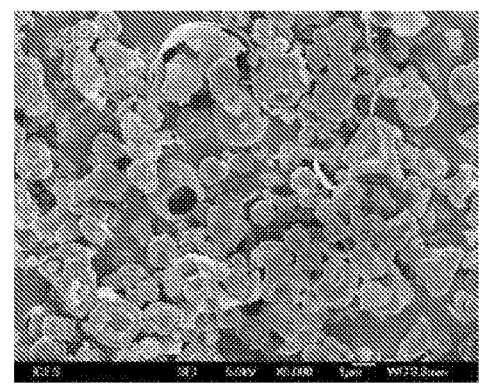

[Fig. 2]
e)
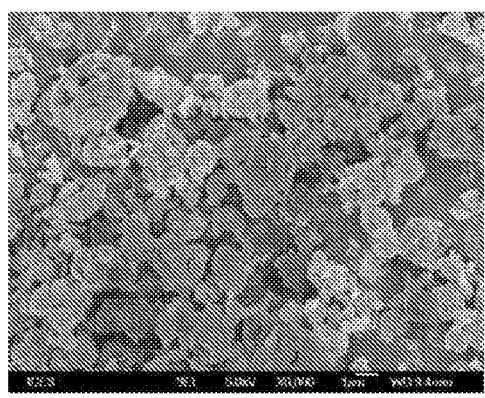
f)
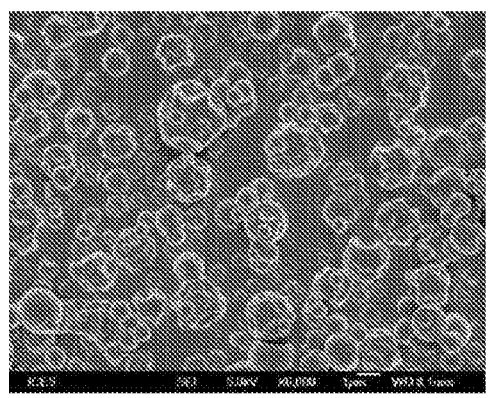
g)
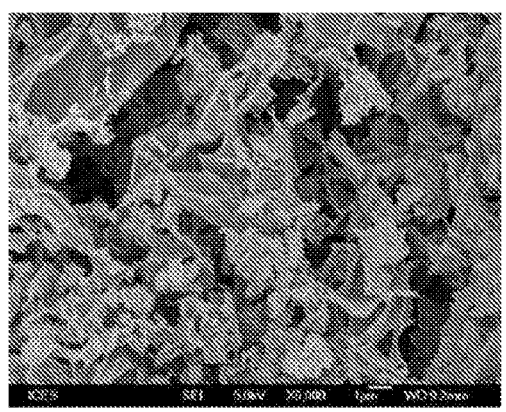

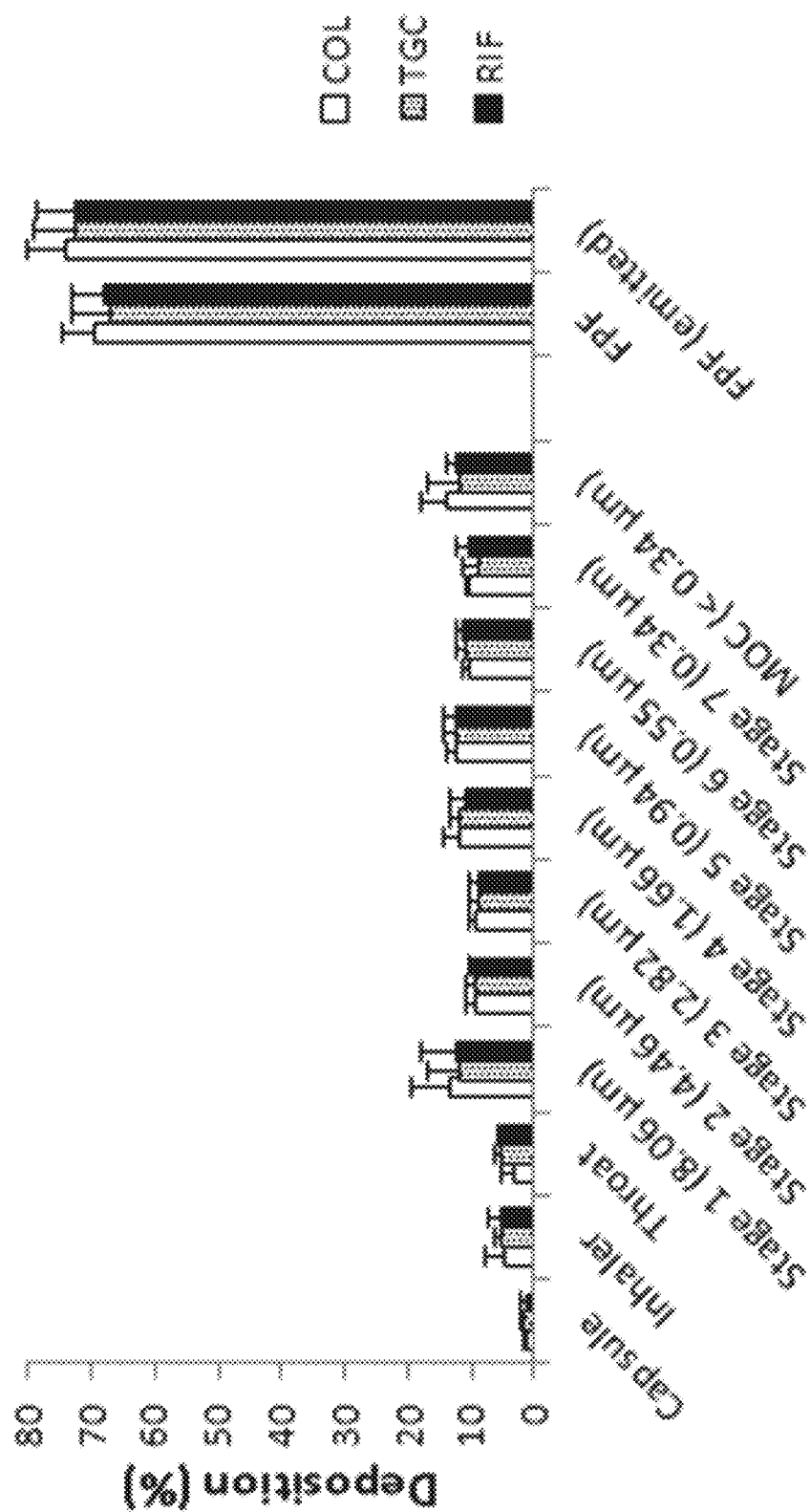
[Fig.3]

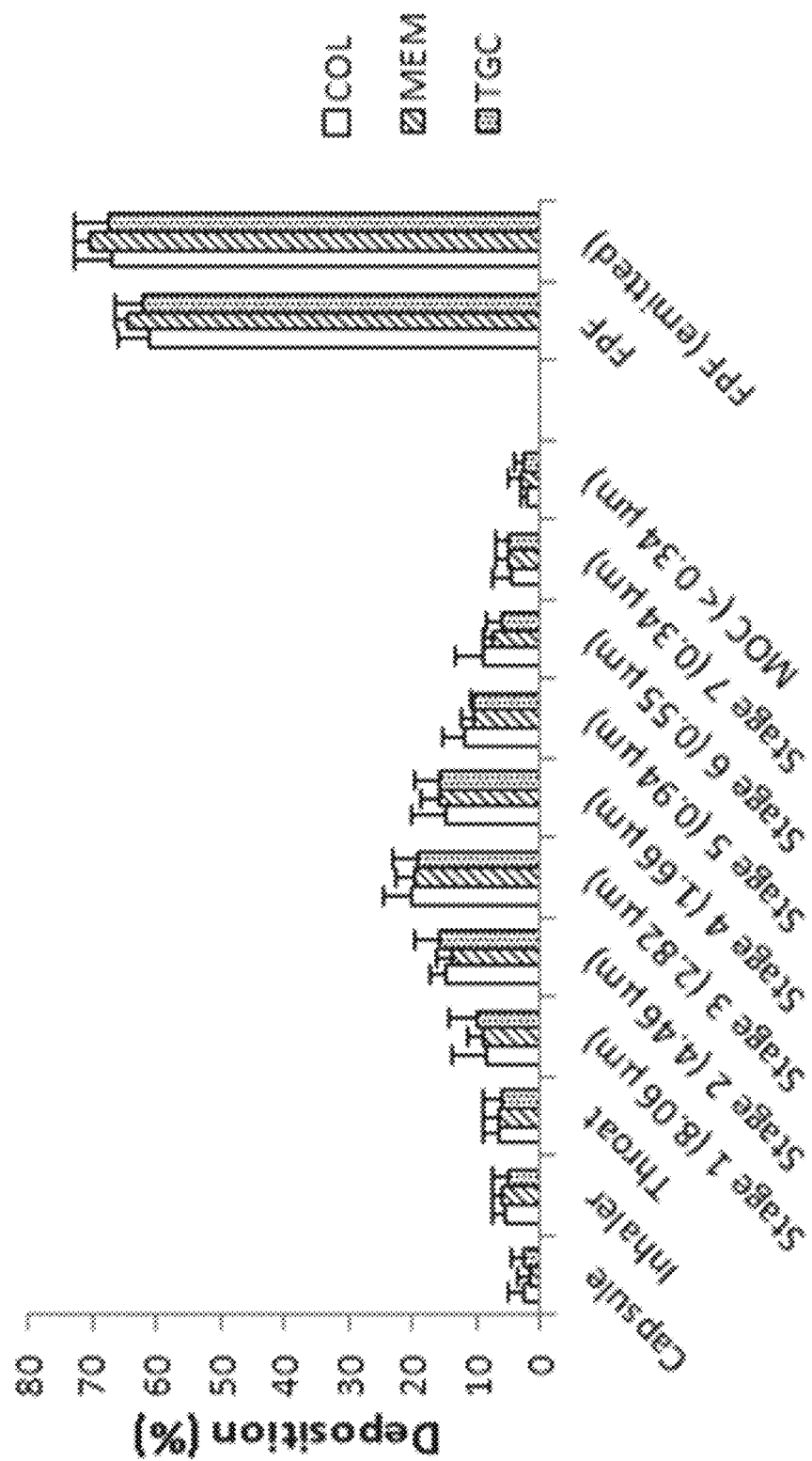
[Fig.4]

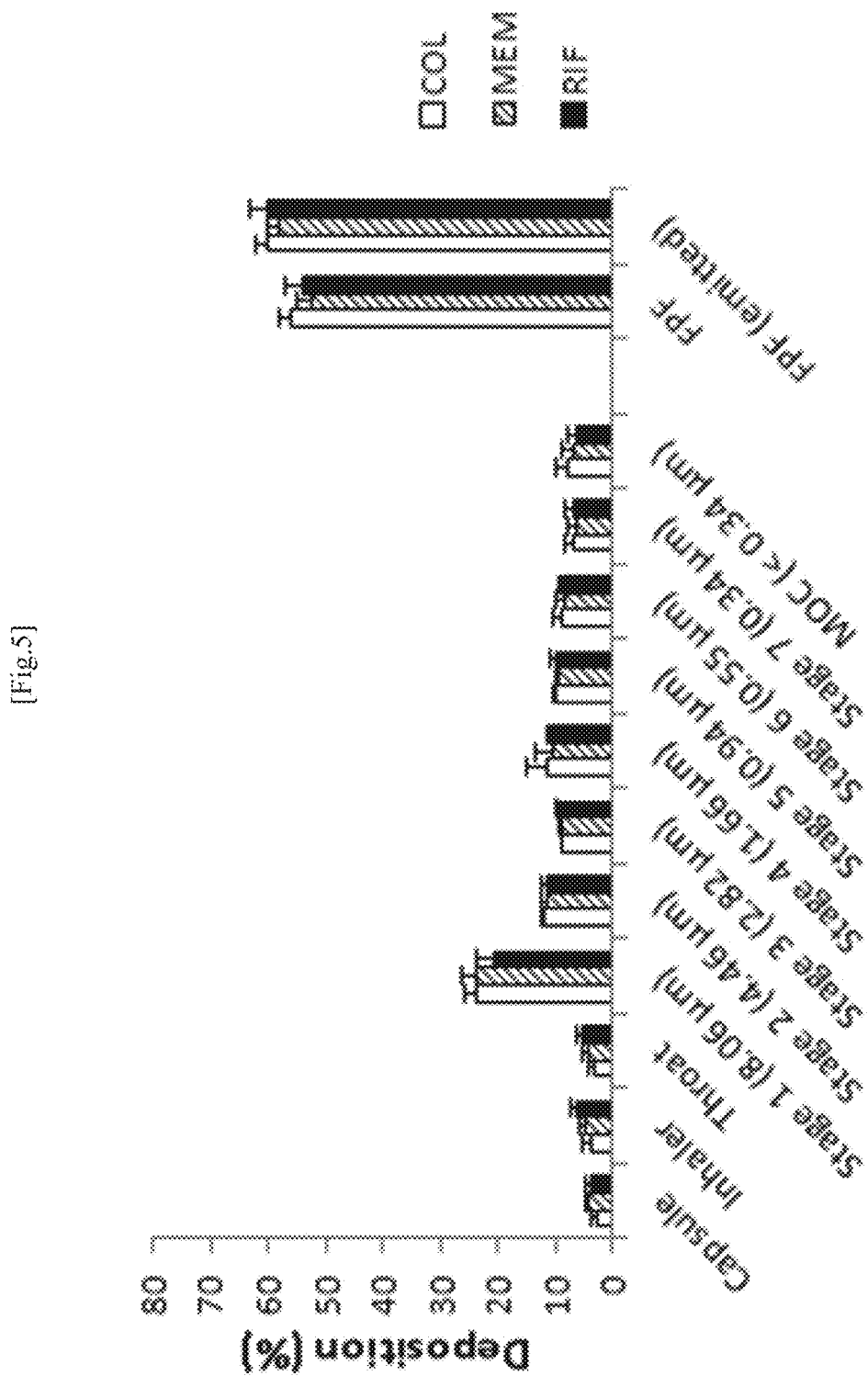
[Fig.5]

[Fig. 6]
a)
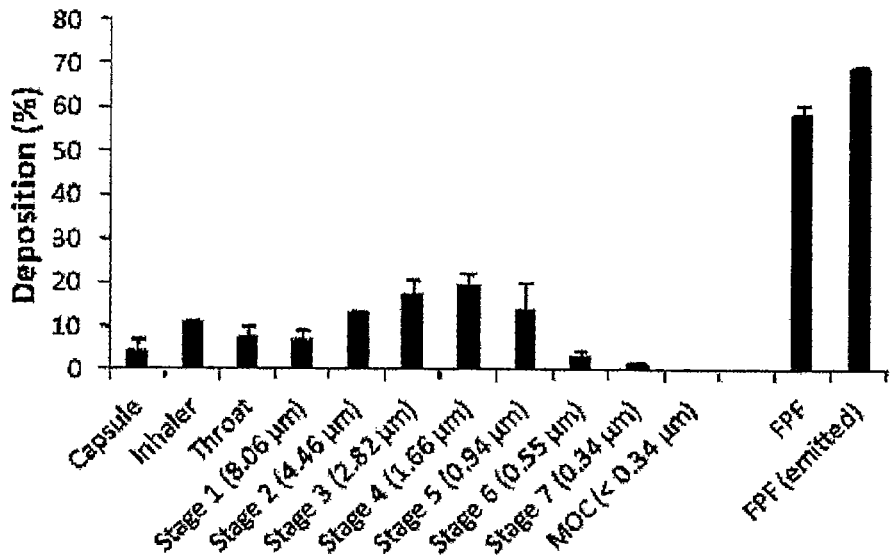
b)
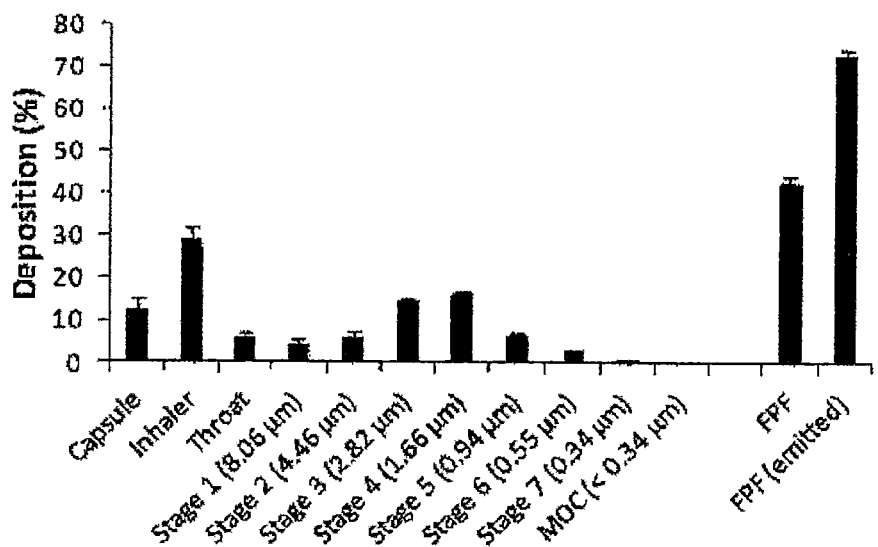

[Fig. 6]
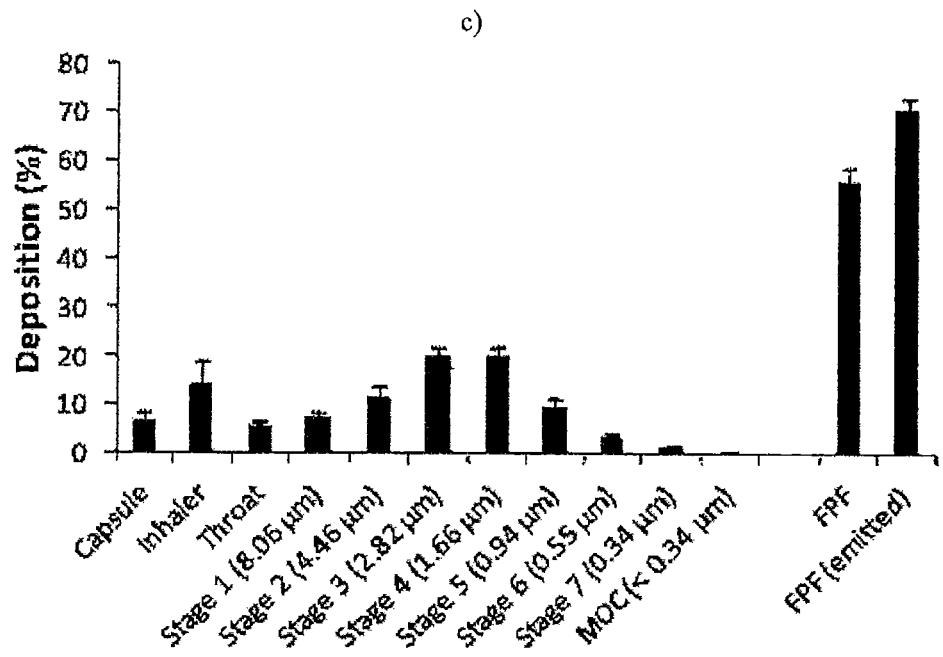
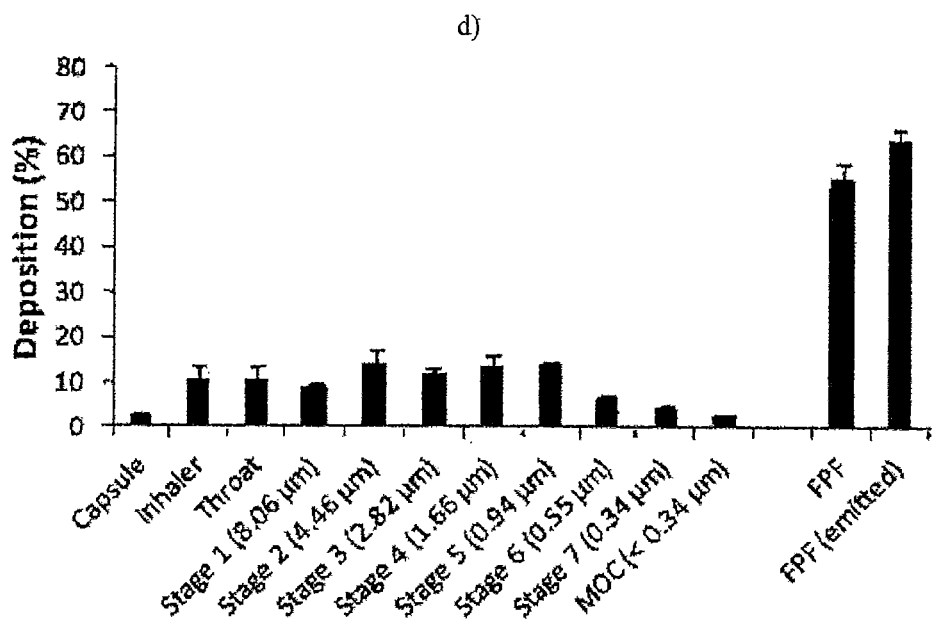

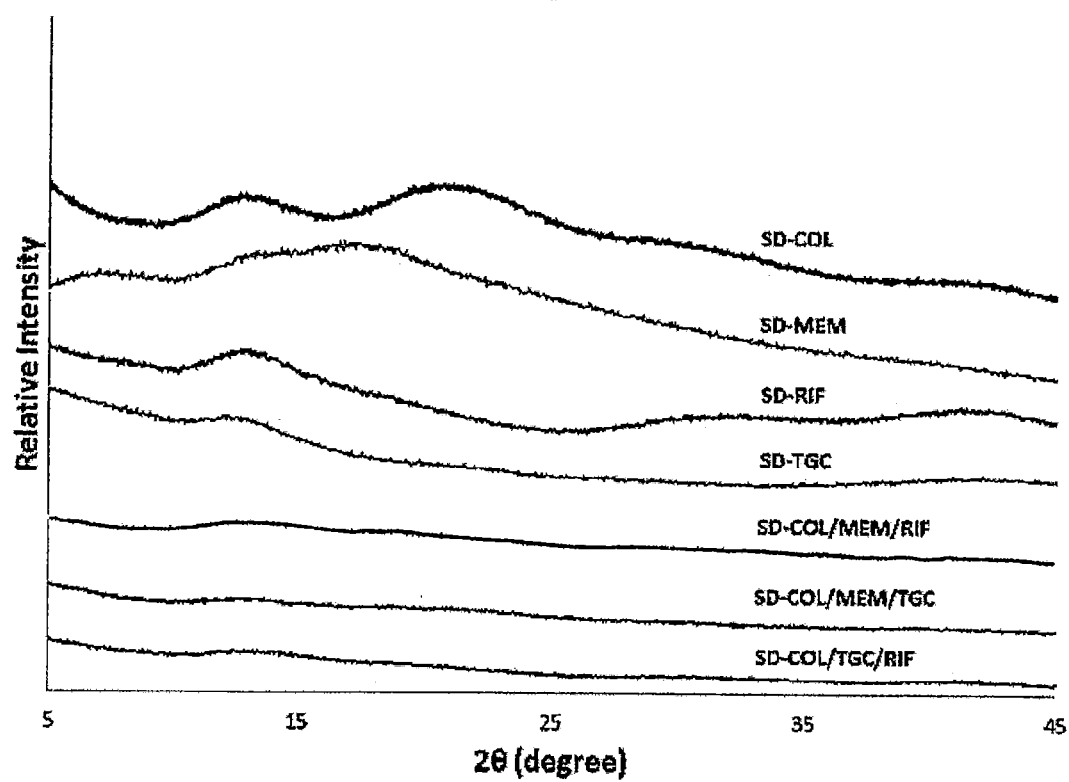
[Fig. 7]

ANTIBIOTIC COMPOSITIONS FOR TREATING BACTERIAL INFECTIONS

CROSS-REFERENCE TO RELATED APPLICATIONS

This patent application is a divisional of U.S. patent application Ser. No. 15/329,244, filed Jan. 25, 2017, which is a U.S. National Phase Application under 35 U.S.C. § 371 of International Application No. PCT/SG2015/050235, filed 24 Jul. 2015, entitled ANTIBIOTIC COMPOSITIONS FOR TREATING BACTERIAL INFECTIONS, which claims the benefit of priority of Singapore Patent Application No. 10201404407X, filed 25 Jul. 2014, the contents of which were incorporated by reference in their entirety for all purposes.

TECHNICAL FIELD

The present invention generally relates to the fields of microbiology, biotechnology, and inhalation aerosols. More specifically, the present invention relates to dry powder compositions for the treatment of bacterial infections, such as multi-drug resistant bacterial infections.

BACKGROUND ART

Respiratory lung infections due to multidrug resistant pathogens are increasing worldwide. Their multidrug resistance profile makes currently available therapeutic options extremely limited. Some of these pathogens include methicillin-resistant *Staphylococcus aureus* (MRSA), multidrug-resistant *Streptococcus pneumoniae*, and vancomycin-resistant enterococci (VRE) among the Gram-positive bacteria; and multidrug-resistant *Acinetobacter baumannii*, *Pseudomonas aeruginosa* and Enterobacteriaceae (including *Klebsiella pneumoniae* and *Escherichia coli*), among the Gram-negative bacteria.

In view of the rising bacterial resistance rates worldwide, there is an anticipated demand for novel antibiotic compositions to broaden the antimicrobial spectrum, improve the efficacy, prevent the emergence/re-emergence of resistant bacteria, and lower the dose of the individual drugs to reduce the side effects as well as the treatment costs.

The development of resistance to antibiotics is well-documented for both Gram-negative bacteria and Gram-positive bacteria, which has implications in the ability to treat pulmonary infections and respiratory diseases that afflict millions of people across the world leading to suffering, economic loss and premature death. In particular, Gram-negative bacteria are more resistant to antibiotics than Gram-positive bacteria due to the presence of a second outer membrane, which provides an efficient barrier to both hydrophilic and hydrophobic compounds. Consequently, Gram-negative bacterial infections are typically more problematic to treat in view of the fewer classes of antibiotics available for effective treatment.

As carbapenems (for example, imipenem, meropenem and doripenem) possess broad-spectrum activity against many Gram-negative bacteria they remain the 'final-line' drug of choice for extended-spectrum, β-lactamase-producing organisms. However, the increasing prevalence of carbapenem-resistant and carbapenemase-producing organisms is jeopardizing the efficacy of carbapenems (carbapenem-resistant bacteria are "superbugs", exhibiting broad resistance to many other antibiotic classes, often leaving the infection untreatable). Hence, seeking alternative treatment regimens has become a pressing issue.

Currently, colistin (a 50-year old polymyxin class of antibiotics), is undergoing a period of revival, and is favored as a 'last line' therapeutic against these hard to treat multi-drug-resistant bacteria, such as *P. aeruginosa*, *A. baumannii* and *K. pneumoniae*. Unfortunately, in recent years, sporadic reports of colistin-resistant strains have started emerging from various parts of the world (for example, Singapore, Greece, Israel and South Korea).

Combination regimens are therefore attractive alternative strategies to overcoming these rising rates of drug resistance in the dearth of newer antibiotics. Inhaled delivery of these combination compounds are useful in eradicating these pathogens more effectively due to direct lung targeting at high minimum inhibitory concentrations (MICs). The simultaneous use of multiple classes of antibiotics is also useful in protecting against the re-emergence of drug resistant bacteria.

As such, there is a need in the art for antibiotic compositions that are effective in the treatment of infections by multi-drug resistant bacteria, and the subsequent reduction in the prevalent rates of drug resistance.

SUMMARY OF INVENTION

In one embodiment, there is provided a dry powder composition comprising: a polymyxin antibiotic; and at least one further antibiotic selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic.

In another embodiment, there is provided the use of a dry powder composition as described herein in the manufacture of a medicament for treating a subject infected, suspected to be infected, or at risk of infection, with a multidrug resistant bacterium.

In another embodiment, there is provided the use of a dry powder composition as described herein in the manufacture of a medicament for treating a respiratory system infection by a bacterium.

In another embodiment, there is provided the use of a dry powder composition as described herein in the manufacture of a medicament for treating a pulmonary disease or condition.

BRIEF DESCRIPTION OF DRAWINGS

The invention will be better understood with reference to the detailed description when considered in conjunction with the non-limiting examples and the accompanying drawings, in which:

FIG. 1 shows the different mechanisms of action of the antibiotic combinations of the present invention.

FIG. 2 shows the Field Emission Scanning Electron Microscopy (FESEM) images of the spray dried powders of a) SD-COL/TGC/RIF; b) SD-COL/MEM/TGC; c) SD-COL/MEM/RIF; d) SD-COL; e) SD-TGC; f) SD-MEM and g) SD-RIF. COL=colistin; MEM=meropenem; TGC=tigecycline; RIF=rifampicin; GEN=gentamicin and SD=spray dried.

FIG. 3 shows In vitro deposition of the co-spray dried ternary formulation SD-COL/TGC/RIF at 60 L/min of airflow. NGI=Next Generation Impactor; Stages 1-7=impactor stages, with the corresponding aerodynamic cutoff diameter in parentheses; MOC=NGI micro-orifice collector.

FIG. 4 shows In vitro deposition of the co-spray dried ternary formulation SD-COL/MEM/TGC at 60 L/min of airflow. NGI=Next Generation Impactor; Stages 1-7=impactor stages, with the corresponding aerodynamic cutoff diameter in parentheses; MOC=NGI micro-orifice collector.

FIG. 5 shows In vitro deposition of the co-spray dried ternary formulation SD-COL/MEM/RIF at 60 L/min of airflow. NGI=Next Generation Impactor; Stages 1-7=impactor stages, with the corresponding aerodynamic cutoff diameter in parentheses; MOC=NGI micro-orifice collector.

FIG. 6 shows In vitro deposition of the spray dried individual species at 60 L/min of airflow. (a) SD-COL. (b) SD-MEM, (c) SD-TGC, (d) SD-RIF. NGI=Next Generation Impactor; Stages 1-7=impactor stages, with the corresponding aerodynamic cutoff diameter in parentheses; MOC=NGI micro-orifice collector.

FIG. 7 shows the X-Ray diffraction patterns of SD-COL/MEM/RIF, SD-COL/MEM/TGC, SD-COL/TGC/RIF and their spray-dried individuals.

DEFINITIONS

The following are some definitions that may be helpful in understanding the description of the present invention. These are intended as general definitions and should in no way limit the scope of the present invention to those terms alone, but are put forth for a better understanding of the following description.

As used herein, the term "composition" in the context of the present invention refers to a combination of antibiotics optionally containing other components, such as carriers, excipients, diluents, isotonic solutions, buffers and the like. The term "formulation" means a specific composition formulated for specific use, such as for aerosolization of an antibiotic in either the dry powdered, solution or suspension form.

As used herein, the term "antibiotic" refers to a natural or synthetic substance that has the capacity to inhibit the growth of, or to kill other microorganisms. As used herein, the term "microorganism" refers to prokaryotic and eukaryotic cells, which grow as single cells, or when growing in association with other cells, do not form organs (for examples microorganisms include bacteria, yeast, molds, and fungi).

As used herein, the language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention.

As used herein, the term "treatment" refers to any and all uses which remedy an infection, disease state or symptoms, prevent the establishment of disease, or otherwise prevent, hinder, retard, or reverse the progression of an infection or disease or other undesirable symptoms in any way whatsoever. The terms "treat," or "treating," refers to administering a medicament for prophylactic and/or therapeutic purposes. The term "prophylactic treatment" refers to treating a subject who is not yet infected, but who is susceptible to, or otherwise at risk of, a particular infection such that there is a reduced onset of infection. Treatment may eliminate the infection, or it may reduce the bacterial load in the tissues that results in improvements measured by a subject's symptoms or measures of lung function.

As used herein, the term "bacterial infection" refers to the undesired proliferation or presence of invasion of bacteria in a host organism or subject. This includes the excessive growth of bacteria that are normally present in or on the body of a mammal or other organisms. More generally, a bacterial infection can be any situation in which the presence of a bacteria population(s) is damaging to a subject. Thus, a bacterial infection exists when excessive numbers of a bacterial population are present in or on a subject's body, or when the effects of the presence of a bacterial population(s) is damaging the cells or other tissue of a subject.

As used herein, the term "drug resistant" when used in reference to bacterium refers to a bacterium that is resistant to the antimicrobial activity of a drug, such as an antibiotic. Drug resistance may also be referred to as antibiotic resistance. In some cases, a bacterium that is generally susceptible to a particular antibiotic can develop resistance to the antibiotic, thereby becoming a drug resistant bacterium. A "multi-drug resistant" bacterium is one that is resistant to more than one drug having antimicrobial activity. One skilled in the art can readily determine if a microbe is drug resistant using routine laboratory techniques that determine the susceptibility or resistance of a bacterium to a drug or antibiotic.

As used herein, the term "synergistic effect" refers to a larger therapeutic effect of the combined antibiotics of the formulations disclosed in comparison to the effect predicted from the sum of each antibiotic alone.

DETAILED DESCRIPTION

The present invention provides a novel antibiotic composition for the treatment of bacterial infections, respiratory diseases and pulmonary infections. More particularly, the present invention and antibiotic composition represents a novel and timely intervention in the fight against multi-resistant bacteria.

I. Antibiotic Composition

Antibiotics that may be used in the present invention include, but are not limited to broad-spectrum antibiotics (for example, tetracyclines); medium-spectrum antibiotics (for example, bacitracin, erythromycins, penicillin, cephalosporins and streptomycins); and narrow spectrum antibiotics (for example, antibiotics that are effective against only a few species of bacteria, for example, polymyxins).

In particular, the antibiotics that may be used in the present invention are selected from an antibiotic family or class including but not limited to aminoglycoside, ansamycin, carbacephem, carbapenem, cephalosporin, glycopeptide antibiotic, lincosamide, lipopeptide, macrolide, monobactam, nitrofuran, oxazolidonone, penicillin, polymyxin, polypeptide antibiotic, quinolone, sulfonamide, tetracycline, chloramphenicol, phosphonic acid antibiotic and mycobacteria antibiotic. The antibiotic families described herein and their specific subclasses of antibiotics are well defined and known in the art by the skilled artisan. Nevertheless, the following non-limiting examples of specific antibiotics that are categorized under each family are defined in the below Table 1.

TABLE 1

| Antibiotic Family/Class | Specific Antibiotics |
|---|---|
| aminoglycoside | neomycin, amikacin, kanamycin, streptomycin and tobramycin |
| ansamycin | Rifamycin, rifaximin, rifapentine, rifabutin, rifampicin, naphthomycins, geldanamycin, ansamitocin and streptovaricins |
| carbacephem | A class of synthetic antibiotics, based on the structure of cephalosporin, a cephem. Carbacephems are similar to cephems, but with a carbon substituted for the sulfur, for example Loracarbef |
| carbapenem | Imipenem, doripenem, ertapenem and meropenem |
| cephalosporin | cephalexin, cefadroxil, cefdinir, cefoxitin, cefaclor, ceftaroline and cefixime |
| glycopeptide | A class of drugs of microbial origin that are composed of glycosylated cyclic or polycyclic nonribosomal peptides, and may include but not limited to vancomycin, teicoplanin, telavancin, ramoplanin and decaplanin |
| lincosamide | clindamycin and lincomycin |
| lipopeptide | daptomycin |
| macrolide | azithromycin, clarithromycin, dirithromycin, erythromycin, roxithromycin, troleandomycin, telithromycin, spiramycin |
| monobactam | aztreonam |
| nitrofuran | furazolidone, nitrofurantoin |
| oxazolidonone | Linezolid, posizolid, radezolid, torezolid |
| penicillin | amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin |
| polymyxin | colistin, polymyxin B |
| polypeptide | Bacitracin |
| Quinolone | Ciprofloxacin, Nadifloxacin, Levofloxacin, Moxifloxacin, Sparfloxacin and Gatifloxacin |
| Sulfonamide | co-trimoxazole, dapsone, silver sulfadiazine, mafenide, sulfacetamide. |
| tetracycline | doxycycline, minocycline, tigecycline, demeclocycline, oxytetracycline, tetracycline analogues |
| Chloramphenicol | chloramphenicol. |
| phosphonic acid | fosfomycin |
| Anti-mycobacterial | streptomycin, clofazimine, capreomycin, dapsone, D-cycloserine, ethambutol, ethionamide, isoniazid, pyrazinamide, rifampin, rifabutin, rifapentine |

As it will be appreciated, analogues or variants of the antibiotics listed in Table 1 may be used in the present invention. These antibiotics may be referred to as "functional analogues or variants" that maintain the antibiotic activity as compared to the reference antibiotic. The functional analogue or variant antibiotics may be found in nature or be an engineered mutant thereof. Moreover, the antibiotic activity of the analogues or variants may be readily determined by well-known methods and techniques in the art.

In accordance with the present invention, two or more antibiotics may be used in combination. In another embodiment, three or more antibiotics may be used in combination, and preferably three antibiotics may be used in combination. A combination of three antibiotics may be referred to as a ternary drug combination.

In this regard, the combination of antibiotics is formulated into a composition.

Thus, the present invention provides a composition comprising at least two or at least three antibiotics selected from the group consisting a polymyxin, an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic.

In one embodiment, an antibiotic comprised in the composition is a polymyxin. Accordingly, in one embodiment, the composition comprises a polymyxin antibiotic; and at least one further antibiotic selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic.

In one embodiment, the polymyxin is colistin (polymyxin E). In one embodiment, the colistin is colistin sulphate.

In another embodiment, the at least one further antibiotic is selected from the group consisting of a carbapenem, an ansamycin and a tetracycline.

In one embodiment, the carbapenem is selected from the group consisting of ertapenem, doripenem, imipenem and meropenem. In a preferred embodiment, the carbapenem is meropenem.

In one embodiment, the ansamycin is rifampicin.

In one embodiment, the tetracycline is selected from the group consisting of demeclocycline, doxycycline, minocycline, oxytetracycline and tetracycline analogues. In a preferred embodiment, the tetracycline is tigecycline.

In one embodiment, the composition comprises three antibiotics. As such, in one embodiment, the composition comprises a polymyxin antibiotic, an ansamycin antibiotic and a tetracycline antibiotic. In a preferred embodiment, the composition comprises colistin, tigecycline and rifampicin.

In another embodiment, the composition comprises a polymyxin antibiotic, a tetracycline antibiotic and a carbapenem antibiotic. In a preferred embodiment, the composition comprises colistin, meropenem and tigecycline.

In another embodiment, the composition comprises a polymyxin antibiotic, an ansamycin antibiotic and a carbapenem antibiotic. In a preferred embodiment, the composition comprises colistin, meropenem and rifampicin.

II. Additional Components

The composition may be formulated with one or more components. The selection of the one or more components may be readily chosen by the skilled artisan based upon the formulation of the composition and route of administration. The suitability of the one or more components may be readily known by those skilled in the art or may be determined using well-known techniques. The one or more components may comprise excipients, antibiotics, a pharmaceutically acceptable carrier, a mucolytic agent, an anti-inflammatory agent, or pharmaceutically active ingredients.

For example, if the composition is formulated as a dry powder formulation that is to be administered using a dry powder inhaler, the composition may comprise one or more components which are commonly used in the preparation of a dry powder formulation, such as an excipient. Thus, in one embodiment the one or more components may comprise an excipient. In general, excipients are used to enhance the physical or chemical stability of the active ingredient, and its mechanical properties, and/or its pharmaceutical properties, such as dissolution and permeation. In dry powder formulations, excipients function as carrier particles to reduce drug cohesiveness by occupying the high-energy sites of the drug particles. Examples of carrier particles may include sugars or sugar alcohols such as mannitol, lactose, glucose, sorbitol, trehalose, raffinose or dextrose. Usually, no more than a few milligrams of a drug need be delivered, and excipients provide bulk, which improves handling, dispensing, and metering of the drug. Other excipients may be phospholipids, such as phosphatidylcholine and cholesterol; lubricants that reduce drug cohesion and adhesion, such as leucine, magnesium stearate, sodium stearate, polyethylene glycol; polymers that act as drug release modifiers or formulation stability enhancers, such as chitosan, polyvinyl alcohol, polylactic-co-glycolic acid; sugar polymers, such as dextran, dextrin; or stabilizers, such as tocopherol, cyclodextrins, polymers, albumins, antioxidants, surfactants and salts. Excipients may make up over 99% of the dry powder inhaler formulation by weight. Physiochemical properties of the excipient such as size and morphology may affect the performance of the dry powder formulation. The adhesive forces of the formulation may also be considered, wherein inadequate separation of the active ingredient and carrier is the main reason for deposition problems. Thus, the excipient may be modified before combining it with the compositions of the present invention. It should also be appreciated that excipients are not always required.

In another embodiment, the one or more components may comprise a mucolytic agent and/or an anti-inflammatory agent. A mucolytic agent helps to loosen and clear mucus from an airway that has been infected by a bacteria or virus. The mucolytic agent may include a lysozyme, ambroxol hydrochloride, sodium chloride, N-acetylcysteine, or mannitol. An anti-inflammatory agent reduces infection severity and may include a steroid or a non-steroidal anti-inflammatory drug, such as aspirin, ibuprofen, naproxen. It is also possible to use more than one mucolytic agent or anti-inflammatory agent in the composition.

In another embodiment, the one or more components may comprise pharmaceutically active ingredients. For example, the formulation may comprise a pharmaceutical composition used for treating lung cancer, steroids (for example, budesonide), beta-2-agonists (for example, salbutamol sulphate), anticholinergics (for example, ipratropium bromide), mucolytic agents (for example, lysozyme, ambroxol hydrochloride), substances added to improve wound healing (for example, heparin), anti-histimine (for example, cetrizine hydrochloride) or decongestants (for example, pseudoephedrine).

In another embodiment, the one or more components may comprise anti-fungal agents to target mixed pathogen populations. The anti-fungal agents may include but are not limited to polyene anti-fungal agents (for example, Amphotericin B, Nystatin or Pimaricin), azole anti-fungal agents (for example, Posaconazole, Voriconazole, Fluconazole or Itraconazole), or Echinocandin anti-fungal agents (for example, Caspofungin, Micafungin or Anidulafungin).

In another embodiment, the one or more components may comprise anti-cancer drugs for concurrent cancer, and bacterial or mixed infection therapy, whereby a weakened immune system and hence an increased risk for pathogenic infections is a common occurrence during the cancer treatment. The anti-cancer drugs may include but are not limited to Cisplatin, Paclitaxel, Doxurubicin, Methotrexate, Carboplatin or Gemcitabine.

In another embodiment, the one or more components may comprise a pharmaceutically acceptable carrier. The carrier may include, for example, one or more of the following: suspension aids, desiccants, diluents, stabilizers, glidants, binders, fillers and bulking agents, and the like. The filler material and hulking agents may comprise about 10 to 95% of the composition. In a preferred embodiment, the filler(s) will make up about 60 to 85% of the composition. Filler material can include any inert pharmaceutical bulking agent or material.

Preferably, microcrystalline cellulose is utilized. Also highly efficacious is mannitol as a filler/bulking agent. Silicon dioxide also has excellent bulking properties. It is desirable that a combination of microcrystalline cellulose, mannitol and silicon dioxide be provided.

As such, in one embodiment the composition disclosed herein may comprise one or more components selected from the group consisting of excipients, antibiotics, a pharmaceutically acceptable carrier, a mucolytic agent, an anti-inflammatory agent, and pharmaceutically active ingredients. In one embodiment, the one or more components is suitable for oral or nasal administration.

III. Dry Powder Composition

The compositions described herein may be prepared in the form of a dry powder. Accordingly, in one embodiment the composition described herein is a dry powder composition.

The composition described herein may be milled, precipitated, spray dried or otherwise processed to particle sizes between about 1 and 5 μm in preparing the dry powder composition. In particular, the composition described herein may be prepared to a powder having particles with volume median diameters ($d_{50}$) ranging from 1-10 μm, more preferably 0.1-7 μm, 0.1-5 μm or 0.5-5 μm, by media milling, jet milling, spray drying or particle precipitation techniques that are readily known in the art. As such, in one embodiment the volume median diameter ($d_{50}$) of the particles in the dry powder composition is in the range of 0.5-10 μm, and preferably in the range of 1-5 μm. In one embodiment, the dry powder composition is prepared by spray-drying. The technique of spray-drying uses methods conventionally known in the art and involves spraying a fine mist of the composition through a nozzle and into a hot vapor stream. The particles are dried in the process and are then collected.

It will be readily appreciated by the skilled artisan that techniques suitable for preparation of dry powders and any and all improvements thereof are intended to be within the scope of the invention.

As such, in one embodiment, the present invention provides a dry powder composition comprising a polymyxin antibiotic; and at least one further antibiotic selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic.

Any effective weight ratio of the antibiotics in the composition may be used. The weight ratio of the antibiotics in the dry powder composition will depend on the particular dosing regimen, and how much of each of the particular antibiotics is to be included in the final dose.

In one embodiment, the weight ratio of the polymyxin antibiotic to the at least one further antibiotic may be in the range from about 1:5 to about 5:1; or from about 1:1 to about 2:1, preferably from about 1:4 to about 4:1, more preferably from about 1:3 to about 3:1. In one embodiment, the weight ratio of the polymyxin antibiotic to the at least one further antibiotic may be 5:4 or 5:12.

In another embodiment, the dry powder composition comprises three antibiotics. In one embodiment, the dry powder composition comprises a polymyxin antibiotic, an ansamycin antibiotic and a tetracycline antibiotic in a weight ratio of about 5:4:12. In one embodiment, the dry powder composition comprises colistin, tigecycline and rifampicin in a weight ratio of about 5:4:12.

In another embodiment, the dry powder composition comprises a polymyxin antibiotic, a tetracycline antibiotic and a carbapenem antibiotic in a weight ratio of about 5:4:4.

In a preferred embodiment, the dry powder composition comprises colistin, meropenem and tigecycline in a weight ratio of about 5:4:4.

In another embodiment, the dry powder composition comprises a polymyxin antibiotic, an ansamycin antibiotic and a carbapenem antibiotic in a weight ratio of about 5:4:12. In a preferred embodiment, the dry powder composition comprises colistin, meropenem and rifampicin in a weight ratio of about 5:4:12.

In one embodiment, the dry powder compositions of the present invention and antibiotic combinations may exhibit a therapeutic effect indifferent, additive or larger than the effect predicted from the sum of each antibiotic alone. In one embodiment, the dry powder composition described herein may exhibit a therapeutic effect larger than the effect predicted from the sum of each antibiotic alone. In one embodiment, the dry powder composition described herein exhibits a synergistic effect.

IV. Administration of Dry Powder Composition

Convenient modes of administration of the dry powder composition described herein may include injection (for example subcutaneous or intravenous administration), oral administration, inhalation, or transdermal administration. Depending on the route of administration, the dry powder composition may be coated with a material for protection from the action of enzymes, acids and other natural conditions which may inactivate the therapeutic activity of the compound.

As such, the administration of the dry powder compositions disclosed herein may be via any of the accepted modes of administration including, but not limited to nasal, oral, transdermal, subcutaneous or intravenous. These modes of administration refer to the conventional routes of administration and are readily understood by the skilled artisan based upon the intended use and composition.

In one embodiment, the dry powder composition is formulated to be administered nasally, orally, transdermally, subcutaneously or intravenously. In one embodiment, the dry powder composition is formulated to be administered by an inhaler, a syringe, an implantable device, a medically inserted device or a biomaterial. In particular, the dry powder composition may be reconstituted as an injectable suspension for administration by injection. The implantable device and medically inserted device or biomaterial are those readily known to the skilled artisan for delivery of antibiotics. For example, a medically inserted device may comprise a catheter; and an implantable device or biomaterial may comprise a prosthesis, an artificial heart valve, a breast implant or a dental implant.

In particular, the dry powder compositions described herein may be suitably formulated into solid, semi-solid, liquid and aerosol dosage forms, such as liquids, suspensions, complexations, liposomes or particulates.

In one embodiment, the dry powder compositions may, for example, be prepared as a liquid by dissolving, dispersing, the composition described herein in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. In one embodiment, the dry powder composition is administered by injection. In the case of injectable solutions prepared from the dry powder compositions, the carrier can be a solvent or dispersion medium containing, for example, water, ethanol, polyol (for example, glycerol, propylene glycol, and liquid polyethylene glycol, and the like), suitable mixtures thereof, and vegetable oils.

In another embodiment, the dry powder composition described herein is formulated to be inhaled by the subject either through nasal or oral administration for delivery to a subject's respiratory tract. For administration to the respiratory airways of a subject, the inhalation of the dry powder composition described herein may be via the mouth and throat.

As such, in one embodiment the compositions described herein are dry powder inhalation compositions. In one embodiment, the dry powder composition does not require any further handling such as diluting of the dry powder, and thus is practical and convenient. As such, it is a preferred embodiment that the compositions described herein be prepared as a dry powder inhalation composition with the advantage of being both practical and convenient because it does not require dilution or other handling, it has an extended shelf-life and storage stability and the dry powder inhalation delivery devices are portable and do not require an air compressor needed by aerosol nebulizers.

In particular, the administration of the dry powder inhalation composition to the upper airways may be avoided in favor of the middle and lower airways of the respiratory tract. In one embodiment, the dry powder inhalation compositions may be endobronchially administered for efficacious delivery of the antibiotic composition into the endobronchial space. In this regard, particles of the dry powder compositions having an aerodynamic diameter of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

A dry powder inhalation composition has potency, on a mass basis, which allows delivery of the compositions described herein through the use of a dry powder inhaler. In this regard, the dry powder composition may be administered by devices that are sufficiently small, fully portable and do not require, for example, an air compressor which is needed for a jet nebulizer. Additionally, the dry powder composition has a longer shelf life than liquid compositions for aerosolization.

In one embodiment, the dry powder inhalation composition described herein is administered via an inhalation device. In particular, the dry powder composition may be administered by dry powder inhalers, nebulizers or metered dose inhaler. In relation to the nebulizer and metered dose inhaler the dry powder composition may be reconstituted into a suspension.

In one embodiment, the dry powder inhalation composition described herein is administered via a dry powder inhaler. The dry powder inhaler may be designed for single use or multiple use or as a re-usable or disposable inhaler.

The emitted dose (ED) of the dry powder inhalation composition described herein is the total mass of the antibotics emitted from the inhalation device following actuation. It does not include the material left on the internal or external surfaces of the device, or in the metering system including, for example, the capsule or blister.

The dry powder inhaler may disperse the dry powder formulation at a rate between about 30 to about 100 L/min, 30 to about 80 L/min, 30 to about 70 L/min, 40 to about 90 L/min, 30 to about 60 L/min, 40 to about 70 L/min, 50 to about 70 L/min, 30 L/min, 40 L/min, 50 L/min, 60 L/min or 70 L/min. Administration at these rates can achieve a substantially uniform deposition profile across all impaction stages.

The fine particle dose (FPD) is the total mass of active agent which is emitted from the device following actuation which is present in an aerodynamic particle size smaller than a defined limit. This limit is generally taken to be 5 µm if not expressly stated to be an alternative limit, such as 3 µm, 2 µm or 4 µm. The FPD and ED are both measured using an impactor or impinger, such as a twin stage impinger (TSI), multi-stage liquid impinger (MSLI), Andersen Cascade Impactor (ACI) or a Next Generation Impactor (NGI). Each impactor or impinger has a pre-determined aerodynamic particle size collection cut point for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

The fine particle fraction (FPF) represents the mass fraction of drug particles smaller than 5 µm in the aerosol cloud (FPD) relative to the total mass recovered and may be obtained by interpolation to the cumulative percent undersize at 5 µm. FPF (emitted) may be obtained when the FPD is expressed relative to the ED.

As such, in one embodiment of the present invention, the dry powder inhalation composition has a fine particle fraction (FPF) of at least 30%, at least 35%, at least 40%, at least 45%, at least 50%, at least 55%, at least 60%, at least 65%, or at least 70%. In one embodiment, the dry powder inhalation composition has a fine particle fraction of at least 50%.

The dry powder compositions described herein may be administered with a frequency of about 1, 2, 3, 4, or more times daily, 1, 2, 3, 4, 5, 6, 7 or more times weekly, 1, 2, 3, 4, 5, 6, 7, 8, 9, 10 or more times monthly. In one embodiment, the compositions are administered twice daily. Single or multiple administrations of the compositions according to the invention may be carried out. One skilled in the art would be able, by routine experimentation, to determine effective, non-toxic dosage levels of the composition of the invention and an administration pattern which would be suitable for treating the diseases and/or infections to which the compositions are applicable. Further, it will be apparent to one of ordinary skill in the art that the optimal course of treatment, such as the number of doses of the compound or composition of the invention given per day for a defined number of days, can be ascertained using convention course of treatment determination tests.

V. Treatment of Bacterial Infection

The dry powder compositions described herein may be used to treat bacterial infections in a subject. The subject may be an animal, and in particular a mammal. The term "mammal" is used in its usual biological sense and includes humans, cattle, horses, dogs, and cats, hut also includes many other species.

In this regard, the bacterial infection may be derived from a bacterium selected from the group consisting of *Pseudomonas aeruginosa*, *Pseudomonas fluorescens*, *Pseudomonas acidovorans*, *Pseudomonas alcaligenes*, *Pseudomonas putida*, *Stenotrophomonas maltophilia*, *Aeromonas hydrophilia*, *Escherichia coli*, *Citrobacter freundii*, *Salmonella typhimurium*, *Salmonella typhi*, *Salmonella paratyphi*, *Salmonella enteritidis*, *Shigella dysenteriae*, *Shigella flexneri*, *Shigella sonnei*, *Enterobacter cloacae*, *Enterobacter aerogenes*, *Klebsiella pneumoniae*, *Klebsiella oxytoca*, *Serratia marcescens*, *Morganella morganii*, *Proteus mirabilis*, *Proteus vulgaris*, *Providencia alcalifaciens*, *Providencia rettgeri*, *Providencia swarth*, *Acinetobacter calcoaceticus*, *Acinetobacter baumannii-calcoaceticus* complex, *Acinetobacter haemolyticus*, *Yersinia enter ocolitica*, *Yersinia pestis*, *Yersinia pseudotuberculosis*, *Yersinia intermedia*, *Bordetella pertussis*, *Bordetella parapertussis*, *Bordetella bronchiseptica*, *Haemophilus influenzae*, *Haemophilus parainfluenzae*, *Haemophilus haemolyticus*, *Haemophilus parahaemolyticus*, *Haemophilus ducreyi*, *Pasteurella multocida*, *Pasteurella haemolytica*, *Helicobacter pylori*, *Campylobacter fetus*, *Campylobacter jejuni*, *Campylobacter coli*, *Borrelia burgdorferi*, *Vibrio cholera*, *Vibrio parahaemolyticus*, *Legionella pneumophila*, *Listeria monocytogenes*, *Neisseria gonorrhoeae*, *Neisseria meningitidis*, *Burkholderia cepacia*, *Francisella tularensis*, *Kingella*, and *Moraxella*.

In another embodiment, the bacterium is selected from the group consisting of *Bacteroides fragilis*, *Bacteroides distasonis*, *Bacteroides* 3452A homology group, *Bacteroides vulgatus*, *Bacteroides ovalus*, *Bacteroides thetaiotaomicron*, *Bacteroides uniformis*, *Bacteroides eggerthii*, *Bacteroides splanchnicus*, *Corynebacterium diphtheriae*, *Corynebacterium ulcerans*, *Streptococcus pneumoniae*, *Streptococcus agalactiae*, *Streptococcus pyogenes*, *Streptococcus milleri*; *Streptococcus* (Group G); *Streptococcus* (Group C/F); *Enterococcus faecalis*, *Enterococcus faecium*, *Staphylococcus aureus*, *Staphylococcus epidermidis*, *Staphylococcus saprophyticus*, *Staphylococcus intermedius*, *Staphylococcus hyicus* subsp. *hyicus*, *Staphylococcus haemolyticus*, *Staphylococcus hominis*, *Staphylococcus saccharolyticus*, *Clostridium difficile*, *Clostridium perfringens*, *Clostridium tetini*, and *Clostridium botulinum*.

In another embodiment, the bacterium is an acid-fast bacterium. In one embodiment, the lung bacterium is selected from the group consisting of *Mycobacterium tuberculosis*, and non-tuberculous *Mycobacterium* including *Mycobacterium avium*, *Mycobacterium intracellulare*, *Mycobacterium abscesses* and *Mycobacterium leprae*.

In one embodiment, the bacterium is a Gram-negative bacterium selected from the group consisting of Enterobacteriaceae, *Pseudomonas aeruginosa*, *Acinetobacter baumannii-calcoaceticus* complex and *Mycobacterium* species.

In one embodiment, the bacterium is a Gram-negative bacterium, a Gram-positive bacterium or an acid-fast bacterium. In another embodiment, the bacterium is a multidrug resistant bacterium.

Thus, in one embodiment the present invention provides the use of a dry powder composition described herein in the manufacture of a medicament for treating a subject infected, suspected to be infected, or at risk of infection, with a multidrug resistant bacterium.

A subject may be identified as "infected" or "suspected to be infected" with multidrug resistant bacterium by virtue of the subject having symptoms that are characteristic of a bacterial infection with a bacteria species known to have resistant strains or with a bacteria that is a member of groups that are known to have resistant strains. Alternatively, the bacteria may be isolated from the subject, cultured and identified as a bacteria species known to have resistant strains or a bacteria that is a member of group that are known to have resistant strains.

A subject may be identified as "at risk of infection" with multidrug resistant bacterium by the subject having a wound or a condition or a disease that improves the possibility and occurrence of a bacterial infection, such patients at risk for infection are selected from the group consisting of leukemia patients, lymphoma patients, carcinoma patients, sarcoma patients, allogeneic transplant patients, congenital or acquired immunodeficiency patients, cystic fibrosis patients, and AIDS patients. In another embodiment, a subject may be identified as "at risk of infection" with multidrug resistant bacterium if the subject visits or resides in a location known to be, or likely to be, colonized with multidrug resistant bacterium, such as a medical facility where multi-drug resistant *Staphylococcus aureus* (MDRSA) and multi-drug resistant *Pseudomonas* species may be present. This embodiment may be considered as a prophylactic treatment of a multidrug resistant bacterial infection.

In this regard, the bacterial infection may be a respiratory system infection such as a pulmonary infection. In one embodiment, the present invention provides the use of a dry powder composition described herein in the manufacture of a medicament for treating a respiratory system infection by a bacterium. In one embodiment, the bacterium is a multi-drug resistant bacterium. In one embodiment, the bacterial respiratory system infection is laryngitis, bronchitis, pneumonia, or sinusitis.

In another embodiment, the present invention provides the use of a dry powder composition described herein in the manufacture of a medicament for treating a pulmonary disease or condition. Examples of such disorders can include cystic fibrosis, and chronic obstructive pulmonary disease (COPD), including chronic bronchitis, bronchiectasis and some asthmas. As such, in one embodiment the pulmonary disease or condition is cystic fibrosis, bronchiectasis or chronic obstructive pulmonary disease (COPD).

As it may be appreciated, the dry powder compositions described herein may be applied to a method for treating a bacterial infection in a subject, in particular for treating respiratory system infections. Moreover, the dry powder compositions described herein may be applied to a method for treating a pulmonary disease or condition. In one such embodiment, this method may be used to administer the dry powder composition to the site of infection. Such a method may reduce systemic exposure and maximizes the amount of dry powder composition to the site of bacterial infection.

Accordingly, in one embodiment, the present invention provides a method of treating a subject infected, suspected to be infected, or at risk of infection, with a multidrug resistant bacterium, comprising administering to the subject a dry powder composition as described herein.

In another embodiment, there is provided a method of treating a respiratory system infection by a bacterium in a subject, comprising administering to the subject a dry powder composition as described herein. In one embodiment, the bacterium is a multidrug resistant bacterium. In one embodiment, the multidrug resistant bacterium is selected from the group consisting of *Pseudomonas aeruginosa, Acinetobacter haumannii, Klebsiella pneumonia* and *Escherichia coli*.

In one embodiment, the bacterial respiratory system infection is laryngitis, bronchitis, pneumonia, or sinusitis.

In another embodiment, there is provided a method of treating a pulmonary disease or condition in a subject, comprising administering to the subject a dry powder composition as described herein. In one embodiment, the pulmonary disease or condition is cystic fibrosis, bronchiectasis, or chronic obstructive pulmonary disease (COPD).

The amount of the respective antibiotics in the dry powder compositions to be administered will, of course, be dependent on the subject and disease state being treated, the severity of the affliction, the manner and schedule of administration and the judgment of the prescribing physician.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Working Examples

I. Materials

Meropenem trihydrate and tigecycline were purchased from Afine Chemical (Hangzhou, Zhejiang, China).

Rifampicin was obtained from Leshan Sanjiu-Longmarch Pharmaceuticals Co., Ltd.

Colistin sulfate was purchased from Sigma Chemical Co. (Louis, Mo., USA).

Clinical isolates of multidrug resistant bacteria used in the study were obtained from the National University Hospital, Singapore and included *Pseudomonas aeruginosa* PSE2 (resistant to ciprofloxacin, aminoglycosides, carbapenems), *Klebsiella pneumoniae* ENT443 (resistant to ciprofloxacin and carbapenems), *Escherichia coli* EC424 (resistant to ciprofloxacin, carbapenems), *Acinetobacter baumannii* AB1 (resistant to ciprofloxacin, aminoglycosides, carbapenems), Mueller-Hinton broth (Oxoid, Bashingstoke, UK) was used as the culture media for the antimicrobial activity test.

II. Methods

Preparation of Spray-Dried Powders

Powders of colistin (SD-COL), meropenem (SD-MEM), rifampicin (SD-RIF), tigecyline (SD-TGC), ternary combination powders of colistin/meropenem/rifampicin (SD-COL/MEM/RIF) in weight ratio of 5:4:12, colistin/meropenem/tigecycline (SD-COL/MEM/TGC) in weight ratio of 5:4:4 and colistin/tigecyclinc/rifampicin (SD-COL/TGC/RIF) in weight ratio of 5:4:12 were prepared by spray drying the ethanol-water co-solvent feedstock of antimicrobials agent(s) on a B-90 Nano Spray Dryer (Büchi Labortechnik AG, Flawil, Switzerland) with operating parameters as detailed in table 2. The drug ratios developed were first derived from in vitro susceptibility studies against control strains and guided by EUCAST (European Committee on Antimicrobial Susceptibility Testing) susceptibility breakpoints. The spray-dried powders were stored in a desiccator at room temperature for further characterization. Colistin sulfate (instead of colistimethate sodium) is chosen as colistin sulfate is more stable than colistimethate sodium in human plasma.

TABLE 2

Spray drying parameters

| | |
|---|---|
| Spray mesh size (µm) | 5.5 |
| Feed concentration (w/v %) | 0.65 |
| Co-solvent (DI water:ethanol) ratio (v/v) | 2:1 |
| Nitrogen flow rate (L/min) | 120 |
| Relative spray rate (mL/h) | 4 |
| Inlet Temperature (° C.) | 120 |
| Outlet Temperature (° C.) | 60-65 |
| Yield (%) | 80-90 |

Surface Morphology

The morphology of the powder particles was examined by a field emission scanning electron microscopy (FESEM, JEOL JSM-6700) at 5 kV. Prior to imaging, the samples were dispersed onto carbon sticky tabs and coated with gold for 80 seconds using a sputter coater (Cressington 208HR, Watford, UK).

Particle Size Analysis

The particle size distribution of the spray-dried powders was determined by laser diffraction on the Malvern Mastersizer 2000 (Malvern Instruments, UK) using the Scirocco dry dispersion unit. The powders were dispersed in triplicates at 3 bars of pressure using refractive indices (RI) of 1.575 for SD-COL and SD-COL/MEM/TGC, 1.639 for SD-MEM, 1.675 for SD-TGC, and 1.613 for SD-RIF, SD-COL/MEM/RIF and SD-COL/TGC/RIF.

Powder Crystallinity

Powder crystallinity of the samples was assessed by powder X-ray diffraction (pXRD) at room temperature using an X-ray diffractometer (D8 Advance; Bruker AXS GmbH, Karlsruhe, Germany). Samples were scanned from 5-45° (2θ) with an angular increment of 0.04° and at 1 s per step using Cu $K_\alpha$ radiation generated at 35 kV and 40 mA.

Surface Area Determinations

The specific surface area of the spray-dried powders was determined by a surface area analyzer (Micromeritics ASAP 2420, USA), using nitrogen as the adsorbate gas. Samples were degassed at 25° C. for 24 h on a vacuum dryer, prior to the measurements. The specific surface area was then determined by the multipoint Brunauer-Emmett-Teller (BET) gas adsorption/desorption method.

In Vitro Aerosol Performance

The aerosol performance of the spray-dried powders was assessed using a Next Generation Impactor (NGI, Copley Scientific. Nottingham, UK) coupled with a United States Pharmacopoeia (USP) stainless steel throat in a walk-in environmental chamber (Synersys, Singapore) maintained at 25° C. and 40% RH. The method followed the procedure specified for DPIs in the British Pharmacopoeia (2009). Prior to testing, all the eight impactor stages were sprayed with MOLYKOTE® 316 silicone grease release spray (Dow Corning Corp., Midland, Mich.) to minimize particle bounce. Approximately 10 mg of powder from each formulation was filled into a hydroxypropyl methylcellulose (HPMC) capsule (size 3, Capsugel®, New Jersey, USA), loaded into an Aerolizer® inhaler (Novartis Pharmaceuticals, Basel, Switzerland), pierced and then actuated for 4 s at 60 L/min. Six capsules were fired per experiment, delivering a total dose of 60 mg. The flow through the NGI was measured using a calibrated flow meter (TSI Model 4040C, TSI Instrument Ltd., Buckinghamshire, UK), controlled by a high capacity vacuum pump (Model HCPS, Copley Scientific, Nottingham, UK) and a critical flow controller (TPK 2000, Copley Scientific, Nottingham, UK). After actuation, the device, capsule, throat and each part of the NGI were washed separately and thoroughly using ethanol-water co-solvent. The solutions were then assayed by high performance liquid chromatography (HPLC) after appropriate sample dilutions were made. Each dispersion test was performed in triplicates to obtain mean values. At a flow rate of 60 L/min, the aerodynamic cut-off diameters of stages 1, 2, 3, 4, 5, 6 and 7 are 8.06, 4.46, 2.82, 1.66, 0.94, 0.55 and 0.34 µm. Particles with diameter size less than 0.34 µm were captured on a Micro Orifice Collector (MOC) beyond stage 7.

Fine particle fraction (FPF) represents the mass fraction of drug particles smaller than 5 µm in the aerosol cloud (FPD) relative to the total mass recovered and was obtained by interpolation to the cumulative percent undersize at 5 µm. FPF (emitted) was obtained when the FPD was expressed relative to the ED.

Drug Content Quantification

Drug contents in the spray-dried powders and in the aliquots collected from the NGI were analyzed via HPLC (1100 series, Agilent Technologies, CA, USA). Assay of colistin was conducted via the use of a Zorbax SB C-18 column (4.6 mm×150 mm, 3.5 µm) (Agilent Technologies, CA, USA). The mobile phase consisted of 0.05% (v/v) TFA aqueous solution (solvent A) and acetonitrile (solvent B), delivered at 1 mL/min under a linear gradient: 0-8 min, 80% to 64% A; 8-10 min, 64% A to 80% A. Colistin peak appeared at a retention time of 5.3 min under a UV wavelength of 214 nm. A Zorbax Extend C-18 column (4.6 mm×150 mm, 3.5 µm) (Agilent Technologies, CA, USA) was used as the stationary phase for simultaneous assays of meropenem, tigecyline and rifampicin. The chromatograph separation was performed using a gradient mobile phase system starting with 95:5 solvent A (95% 50 mM ammonium acetate, pH 6.2-5% acetonitrile):B (5% 50 mM ammonium acetate, pH 6.2-95% acetonitrile) changed to 50:50 solvent A:B over 10 min then ramped to 5:95 solvent A:B in 1 min. A 2-min isocratic hold was followed by a step back to the initial conditions. A UV absorbance wavelength of 244 nm was employed for the simultaneous detection of meropenem, tigecyline and rifampicin at retention times of 1.7 and 5.7 and 10.6 min, respectively.

Antimicrobial Activity of Ternary Formulation of Colistin Combinations

In vitro antimicrobial activity of the spray-dried powders was determined quantitatively via time-kill studies. Overnight cultures of the test organism was diluted in Mueller-Hinton broth (MHB) to give a starting bacterial density of approximately $5 \times 10^5$ CFU/ml. Spray-dried powders were added to the cultures such that the final concentrations were at 1×MIC. The cultures were then incubated at 37° C. with shaking. Bacterial cell counts were estimated at time 0 and 24 hr. A synergistic result was defined as a ≥2 $\log_{10}$ decrease in colony count after 24 h by the combination compared to the most active single agent, and additivity as a 1 to <2 $\log_{10}$ decrease in colony count after 24 h by the combination compared to the most active single agent, and indifference as a <1 $\log_{10}$ increase or decrease in colony count after 24 h by the combination compared with that by the most active single agent.

III. Results

The schematic diagram of FIG. 1 illustrates the different mechanisms of action in the representative ternary compositions of the present invention.

TABLE 3

| Individual drug | Drug class | Effect on bacteria | Mode of action | Ternary drug combinations (drug ratio by weight %) |
|---|---|---|---|---|
| Colistin (COL) | Polymyxin | Bactericidal | Disruption of cell membrane | — |
| Meropenem (MEM) | Carbapenem | Bactericidal | Inhibition of peptidoglycan synthesis | COL/MEM/TGC (5:4:4) |
| Rifampicin (RIF) | Ansamycin | Bactericidal | Inhibition of RNA transcription | COL/MEM/RIF (5:4:12) |
| Tigecycline (TGC) | Tetracycline | Bacteriostatic | Inhibition of protein synthesis | COL/TGC/RIF (5:4:12) |

Prior to the present invention, the commercial and conventional antibiotic dry powder inhaler formulations, included Novartis® TIP (Tobramycin Inhaled Powder) and Forest Laboratories® Colobreathe (Colistin Inhaled Powder).

The antibiotic combinations described in table 3, were prepared by co-spray drying the ternary system containing colistin sulphate and two other antibiotics (tigecycline, rifampicin or meropenem trihydrate) and were prepared in the weight ratios illustrated in table 4 using the Nano Spray Dryer B-90. Table 4 illustrates that the antibiotic combinations are shown to be therapeutically effective against multi-drug resistant *Pseudomonas aeruginosa*, and specifically a synergistic effect was exhibited by the antibiotic combinations.

TABLE 4

| Resistant bacterial strain (Resistance profile) | Drug Ratio | | | | Time-kill assay ($\log_{10}$ change)[a] | Interaction |
|---|---|---|---|---|---|---|
| | COL | MEM | TGC | RIF | | |
| *Pseudomonas aeruginosa* PSE2 (CIP[R]GEN[R]MEM[R]) | | | | | | |
| SD-COL/TGC/RIF | 5 | — | 4 | 12 | −4.0 | Synergy |
| SD-COL/MEM/TGC | 5 | 4 | 4 | — | −3.6 | Synergy |
| SD-COL/MEM/RIF | 5 | 4 | — | 12 | −3.2 | Synergy |

Table 4 legend: COL, colistin; MEM, meropenem; TGC, tigecycline; RIF, rifampicin; GEN, gentamicin.
[a]Values represent the $\log_{10}$ change in CFU/ml in the time kill assay after 24-h exposure to the ternary spray-dried formulations compared to the most active drug.

The ternary dry powder compositions (FIG. 2) consisted of respirable-sized particles ($d_{50}$≈3 μm) capable of achieving high fine particle fractions (FPF) (out of the total dose) of approximately 52-69% and emitted fine particle fractions (FPF(emitted)) of approximately 58-73% (See Table 5 and Table 6).

TABLE 5

| Single component | $d_{50}$ (μm) | Ternary drug combination | $d_{50}$ (μm) |
|---|---|---|---|
| SD-COL | 2.89 ± 0.14 | SD-COL/TGC/RIF | 3.13 ± 0.16 |
| SD-MEM | 1.61 ± 0.06 | SD-COL/MEM/TGC | 3.07 ± 0.28 |
| SD-RIF | 3.23 ± 0.12 | SD-COL/MEM/RIF | 3.43 ± 0.07 |
| SD-TGC | 2.52 ± 0.07 | | |

TABLE 6

| Formulations | FPF [a] (%) | FPF (emitted) [b] (%) |
|---|---|---|
| SD-COL | 58.5 ± 2.1 | 69.4 ± 0.6 |
| SD-MEM | 42.6 ± 1.6 | 73.0 ± 1.4 |
| SD-RIF | 55.1 ± 3.7 | 63.6 ± 2.6 |
| SD-TGC | 56.0 ± 3.2 | 70.9 ± 2.2 |
| SD-COL/MEM/TGC | | |
| COL | 61.2 ± 4.7 | 66.8 ± 6.2 |
| MEM | 64.9 ± 1.6 | 70.4 ± 2.2 |
| TGC | 62.2 ± 4.4 | 67.6 ± 5.2 |
| SD-COL/MEM/RIF | | |
| COL | 55.9 ± 2.0 | 60.1 ± 2.3 |
| MEM | 52.8 ± 2.5 | 58.1 ± 2.1 |
| RIF | 54.2 ± 2.9 | 60.3 ± 2.8 |
| SD-COL/TGC/RIF | | |
| COL | 69.5 ± 5.0 | 73.9 ± 6.1 |
| TGC | 67.2 ± 5.9 | 72.5 ± 6.4 |
| RIF | 67.8 ± 5.3 | 72.7 ± 5.9 |

[a] FPF-fine particle fraction
[b] FPF (emitted)-emitted fine particle fraction
NGI-next generation impactor The results outlined in Tables 5 and 6 show that the composition of the present invention when formulated as a multi-component particle, are able to achieve the 'same particle size' for each drug (i.e. 3 drugs in a single entity), which leads to more uniform drug deposition for each drug, with advantageous implications in terms of therapeutic efficacy.

As illustrated in FIGS. 3-5, a concomitant and uniform in vitro deposition profile is achieved for the antibiotic combinations across all impaction stages when dispersed at 60 L/min. Specifically, the time-kill assay showed a synergism, >−2 $\log_{10}$ change, against resistant *Pseudomonas aeruginosa* for the three ternary combinations in their co-spray dried form, see Table 4.

As it will be appreciated, the above results and three ternary combinations are potentially useful for patients suffering from cystic fibrosis, bronchiectasis, pneumonia and other bacteria-associated respiratory disorders.

Moreover, the three ternary combinations are also shown to be effective (i.e. additive or indifferent interactions) against resistant *A. baumannii, K. pneumoniae* and *E. coli*. In particular, SD-COL/TGC/RIF exhibited a favourable 'additive' interaction against multi-drug resistant *K. pneumonia* and *E. coli*, see Table 7.

In this regard, synergy is defined as a ≥2 $\log_{10}$ decrease in colony count after 24 h by the combination compared to the most active single agent, additivity as a 1 to <2 $\log_{10}$ decrease in colony count after 24 h by the combination compared to the most active single agent and indifference as a <1 $\log_{10}$ increase or decrease in colony count after 24 h by the combination compared with that by the most active single agent.

TABLE 7

| Resistant bacterial strain (Resistance profile) | Drug Ratio | | | | Time-kill assay ($\log_{10}$ change)[a] | Inter-action |
|---|---|---|---|---|---|---|
| | COL | MEM | TGC | RIF | | |
| *Klebsiella pneumoniae* ENT 443 ($CIP^R$ $MEM^R$)* | | | | | | |
| SD-COL/TGC/RIF | 5 | — | 4 | 12 | −1.2 | Additivity |
| SD-COL/MEM/TGC | 5 | 4 | 4 | — | 0.1 | Indifference |
| SD-COL/MEM/RIF | 5 | 4 | — | 12 | 0.0 | Indifference |
| *Escherichia coli* EC424 ($CIP^R MEM^R$)* | | | | | | |
| SD-COL/TGC/RIF | 5 | — | 4 | 12 | −1.0 | Additivity |
| SD-COL/MEM/TGC | 5 | 4 | 4 | — | 0.1 | Indifference |
| SD-COL/MEM/RIF | 5 | 4 | — | 12 | 0.2 | Indifference |
| *Acinetobacter baumannii* AB1 ($CIP^R$ $GEN^R$ $MEM^R$) | | | | | | |
| SD-COL/TGC/RIF | 5 | — | 4 | 12 | −0.5 | Indifference |
| SD-COL/MEM/TGC | 5 | 4 | 4 | — | 0.2 | Indifference |
| SD-COL/MEM/RIF | 5 | 4 | — | 12 | 0.2 | Indifference |

Table 7 legend: COL, colistin; MEM, meropenem; TGC, tigecycline; RIF, rifampicin; CIP, ciprofloxacin; GEN, gentamicin.
*Isolate bears a carbapenemase which results in enzymatic hydrolysis of carbapenems conferring carbapenem resistance.
[a]Values represent the $\log_{10}$ change in CFU/ml in the time kill assay after 24-h exposure to the ternary spray-dried formulations compared to the most active drug.

TABLE 8

| Formulations | Specific surface area (m²/g) |
|---|---|
| SD-COL | 12.97 ± 0.22 |
| SD-MEM | 4.35 ± 0.09 |
| SD-RIF | 51.27 ± 1.71 |
| SD-TGC | 10.34 ± 0.67 |
| SD-COL/MEM/TGC | 10.80 ± 1.64 |
| SD-COL/MEM/RIF | 36.97 ± 0.41 |
| SD-COL/TGC/RIF | 47.48 ± 1.30 |

The ternary spray-dried combination powders presented broad diffused diffraction patterns which are characteristic of amorphous materials (similar to their spray-dried individual species), as shown in FIG. 7. In this regard, it will be appreciated that spray dried powders are typically amorphous.

IV. Discussion

The results described herein, illustrated several benefits of the compositions of the present invention. Firstly, from the microbiological standpoint, the compositions prevent the emergence of bacterial drug resistance as the simultaneous development of resistance towards multiple drug classes is remote; and secondly from a patient management standpoint, combinations comprising colistin have the potential to reduce colistin toxicity by allowing a lowered therapeutic dose. This is achieved via a synergistic or additive interaction of colistin with its partner antibiotics.

When the route of administration of the composition and combination of antibiotics is considered, inhaled delivery of colistin combinations is shown to be effective in eradicating multi-drug resistant (MDR) pathogens as it directly targets the foci of infection. In this regard, elevated drug concentrations can be achieved locally at the site of lung infection without the adverse effects of systemic toxicity. Moreover, a dry powder inhaler (DPI) formulation is superior over the other aerosol delivery modes (for example, a nebuliser or metered dose inhaler (MDI) in terms of stability, delivery efficiency, portability, ease-of-use and the avoidance of undesired precipitation in solutions.

Rifampicin is a bactericidal antibiotic drug of the ansamycin group that has been used to prevent and treat tuberculosis and other infections, but has very limited use in monotherapy that may be due to the rapid emergence of resistance. Meropenem is a member of the carbapenem class of antibiotics that is active against a broad spectrum of Gram-positive and Gram-negative pathogens, including the beta-lactamase producers. However, the worldwide spread of drug resistance to carbapenem antibiotics is seriously threatening this class of life-saving drugs. Tigecycline, had been approved by the Food and Drug Administration (FDA) in 2009 for the treatment of community-acquired pneumonia, and was considered a useful alternative against carbapenem-resistant bacteria. However, its clinical efficacy, especially in severe infections, is problematic, and without being bound by theory may be due to its subdued bacteriostatic action of inhibiting growth, low serum levels and the heightened propensity for resistance development.

Accordingly, the working examples disclosed herein explored the combinations of colistin, rifampicin, meropenem and tigecycline for their potential use as combinational therapies. In this regard, spray-dried ternary combination particles of these antibiotics were produced, wherein both SD-COL/MEM/RIF and SD-COL/TGC/RIF had crumpled sheet-like structures, whereas SD-COL/MEM/TGC was a mixture of corrugated spherical particles and irregularly-shaped chips (FIG. 2). The similarity in surface morphologies of both SD-COL/MEM/RIF and SD-COL/TGC/RIF to SD-RIF may be due to the dominance of rifampicin in the spray-dried ternary combination particles, which resulted in its prevailing influence on their particle morphologies. The specific surface areas of the ternary spray-dried formulations containing rifampicin (i.e. SD-COL/MEM/RIF and SD-COL/TGC/RIF) were significantly higher than the rifampicin-void spray-dried formulation (i.e. SD-COL/MEM/TGC). This could be due to the former's crumpled sheet-like particle structure, which minimized aggregation and promoted high specific surface areas. For these formulations, the dispersibilities obtained were generally robust (i.e. FPFs ranging from 52.8±2.5% to 69.5±5.0%), thus suggesting the favourability of the corrugated/crumpled particle morphology in aerodynamics. These particles have high free volume with pockets of void space and hence have low densities, are aggregation-resistant, and have reduced inter-particle contact areas.

Airflow of 60 L/min was used to simulate the reduced inspiratory effort achieved by patients with compromised lung functions due to pneumonia or cystic fibrosis as examples. Generally, all the single and ternary spray-dried formulations disclosed herein displayed robust delivery efficiency with FPFs ranging from 42.6±1.6% to 69.5±5.0% (Table 6), wherein an FPF value that is significantly higher than 30% is an index of good aerosol performance. In particular, among the single spray-dried formulations, SD-MEM was found to have a slightly lower FPF of 42.6±1.6% when compared to the others (i.e. FPFs>50%). The lower FPF might be due to the cohesiveness of the powder, which could in a way be inferred by the formulation's high capsule and device retention (i.e. 12.6±2.8% and 29.0±2.9%, respectively (FIG. 6b)). Favourably, when meropenem was formulated as a ternary mix (i.e. SD-COL/MEM/TGC and SD-COL/MEM/RIF), the cohesiveness of meropenem was minimized. Capsule and device retention had decreased significantly to fewer than 5% and 7%, respectively (FIGS. 4 and 5). Clearly, it does seem that formulating the drugs into a ternary mix has the advantage of ameliorating the performance of the poorer-performing species. For the ternary spray-dried formulations (i.e. SD-COL/MEM/TGC, SD-COL/MEM/RIF and SD-COL/TGC/RIF), there was concomitant deposition observed across all stages, including the throat, inhaler and capsule, thus suggesting uniformity in the powder and/or aerosol (FIG. 3-5). Furthermore, all three ternary formulations are highly suited for delivery via the aerosol route in view of the robust FPFs obtained (Table 6). Improvements to the emitted fraction (i.e. inferred via closely similar FPF and FPF (emitted)) were also achieved in the ternary species which again reinforces the benefits of co-delivery.

The antimicrobial activities of the ternary spray-dried powder composition (i.e. SD-COL/MEM/TGC, SD-COL/MEM/RIF and SD-COL/TGC/RIF) were tested against different MDR pathogenic respiratory bacteria and summarized in Tables 4 and 7. In essence, the formulations were all capable of eradicating resistant bacteria. When all three ternary formulations were tested against MDR *Pseudomonas aeruginosa* that was resistant to ciprofloxacin (fluoroquinolone group), gentamicin (aminoglycoside group) and meropenem (carbapenem group), a synergistic kill was obtained across the formulations, with $\log_{10}$ CFU changes of −4.0, −3.6 and −3.2 for SD-COL/TGC/RIF, SD-COL/MEM/TGC and SD-COL/MEM/RIF, respectively, after a 24 h test period. With a synergistic interaction, a much reduced drug dose would be required to achieve the same therapeutic effect as conventional monotherapy.

The above results are applicable to both combinatorial and local delivery strategies (directly to the lungs), which also served to reduce the required drug dose into the body. In totality, a synergistic inhaled combination would not only minimize the toxic side effects of the antibiotics, but also help in the minimization of drug resistance. Although carbapenem-resistant bacteria is currently the bane of patients and medical practitioners worldwide and has limited treatment options, it is nevertheless important to note that meropenem (i.e. a carbapenem) is still relevant and potent in killing these resistant bacteria when applied in a combinatorial composition. Indeed, the results and compositions disclosed herein may have positive implications in terms of extending the drug's useful 'lifespan'. Both SD-COL/MEM/RIF and SD-COL/MEM/TGC (carbapenem(MEM)-containing formulations) could not only eliminate all four species of carbapenem-resistant bacteria, but also elucidate a synergistic response for the MDR *Pseudomonas aeruginosa* isolate.

Among the ternary combination disclosed herein, SD-COL/TGC/RIF (non-carbapenem (MEM)-containing combination) was found to be the best performing species. Not only did this ternary combination exhibit a synergistic interaction against carbapenem-resistant *Pseudomonas aeruginosa*, but also revealed additive interactions against other carbapenem-resistant Gram-negatives such as *Klebsiella pneumoniae* and *Escherichia coli*. Although an additive interaction might be slightly lower than a synergistic interaction, they are nonetheless still useful and advantageous in dosage reduction, which could help in the minimization of the associated side effects and the potential for bacterial resistance.

The superior qualities of SD-COL/TGC/RIF (over SD-COL/MEM/RIF and SD-COL/MEM/TGC) may be attributed to colistin, tigecycline and rifampicin's distinct killing mechanisms which targeted different functions of the bacterial cell (Table 3 and FIG. 1). Bactericidal colistin is a cationic antibiotic that binds to the anionic lipopolysaccharide (LPS) of Gram-negative bacteria's membrane, leading to a disruption of the membrane permeability, leakage of intracellular content and hence cell death. Perturbation of the bacterial cellular membrane integrity by colistin may in turn favour the uptake of tigecycline and rifampicin to effect a 'collaborative' synergistic interaction. Bactericidal rifampicin's mechanism of action is based on its ability to specifically bind and inhibit the bacterial DNA-dependent RNA polymerase.

On the other hand, bacteriostatic tigecycline works by binding to the 30S subunit of the bacterial ribosome, thus inhibiting peptide elongation and subsequently, disrupting protein synthesis. As each of colistin, rifampicin and tigecycline have a unique complementary mode of action that is not shared by any other antibiotic in the combination, it is therefore encouraging to observe a number of favourable interactions arising from the SD-COL/TGC/RIF species, as compared to SD-COL/MEM/RIF and SD-COL/MEM/TGC. For SD-COL/MEM/RIF and SD-COL/MEM/TGC, as they have two antibiotics, meropenem and colistin, with overlapping actions on the bacterial cell wall (FIG. 1), their 'collaborative' efficiency is therefore understandably, slightly lower than SD-COL/TGC/RIF.

Regular use of antibiotics, be it monotherapy or combination therapy, will eventually lead to resistance. The advantage of the present invention and combination of antibiotics lies in the potential for 'rotational therapy' (i.e. treatment rotated between the three different-member combinations). Recalcitrant bacterial infections that require prolonged antibiotic treatment could benefit from such a therapy while enjoying the reduced risk of antimicrobial resistance. With three unique combinations involving three different complementary antibiotics, the possibility of a bacterium developing resistance to all the antibiotics and combinations simultaneously would hence be very far remote.

As such, the present invention and results demonstrated herein provide a 'toolbox' of DPI compositions (for example, COL/TGC/RIF. COL/MEM/RIF and COL/MEM/TGC) to successfully fight against respiratory 'superbugs'. The benefits of co-delivery include the potential for synergy which helps to further lower the toxic drug dose and the associated side effects (i.e. colistin), ameliorating the performance of a poorer-performing species (i.e. meropenem), the life-span extension of 'expiring/redundant' antibiotics (i.e. meropenem, rifampicin and tigecycline) and the opportunity to mount a collaborative and concerted mode of attack on bacteria (i.e. COL/TGC/RIF).

Moreover, compared to nebulised antibiotics, the DPI compositions do not require a bulky nebuliser, are easier and quicker to use, and provide much better formulation stability as it is formulated as a powder. Furthermore, the DPI compositions are capable of a high FPF of ~52-69%, much higher than that achieved via the traditional nebuliser (~10%).

In summary, the compositions of the present invention, and the therapeutic effect of the antibiotic combinations was shown to be advantageous. In addition to the responses against resistant *P. aeruginosa*, the compositions were also capable of killing resistant *A. baumannii, K. pneumonia* and *E. coli* bacteria with either an indifferent or additive interaction. Therefore, the development of the compositions disclosed herein is indeed a novel and timely intervention in the fight against multi-resistant pathogenic respiratory bacteria.

What is claimed is:

1. A process for manufacturing a medicament for treating a subject infected, suspected to be infected, or at risk of infection, with a multidrug resistant bacterium utilizing a dry powder inhaler (DPI) composition of antimicrobial agents comprising: a polymyxin antibiotic; and at least two further antibiotics selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic, wherein the antimicrobial agents are spray dried with a 5.5 μm spray mesh size, and have a particle size of between about 1 and 5 μm.

2. The process of claim 1, wherein the bacterium is a Gram-negative bacteria, optionally wherein the Gram-negative bacteria is selected from the group consisting of, Enterobacteriaceae, *Pseudomonas aeruginosa, Acinetobacter baumannii-calcoaceticus* complex and *Mycobacterium* species.

3. A process for manufacturing a medicament for treating a respiratory system infection by a bacterium utilizing a dry powder inhaler composition of antimicrobial agents comprising: a polymyxin antibiotic; and at least two further antibiotics selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic,
wherein the antimicrobial agents are spray dried with a 5.5 μm spray mesh size, and have a particle size of between about 1 and 5 μm.

4. The process of claim 3, wherein the bacterium is a multidrug resistant bacterium, optionally wherein the multidrug resistant bacterium is selected from the group consisting of *Pseudomonas aeruginosa, Acinetobacter baumannii, Klebsiella pneumonia* and *Escherichia coli*, optionally wherein the bacterial respiratory system infection is laryngitis, bronchitis, pneumonia, or sinusitis.

5. A process for manufacturing a medicament for treating a pulmonary disease or condition utilizing a dry powder inhaler composition of antimicrobial agents comprising: a polymyxin antibiotic; and at least two further antibiotics selected from the group consisting of an aminoglycoside, an ansamycin, a carbacephem, a carbapenem, a cephalosporin, a glycopeptide, a lincosamide, a lipopeptide, a macrolide, a monobactam, a nitrofuran, a oxazolidonone, a penicillin, a polypeptide, a quinolone, a sulfonamide, a tetracycline, a chloramphenicol, a phosphonic acid antibiotic and a mycobacteria antibiotic,
wherein the antimicrobial agents are spray dried with a 5.5 μm spray mesh size, and have a particle size of between about 1 and 5 μm.

6. The process of claim 5, wherein the pulmonary disease or condition is cystic fibrosis, bronchiectasis, or chronic obstructive pulmonary disease (COPD).

7. The process of claim 1, wherein the dry powder inhaler composition is prepared by dissolving the antimicrobial agents in a co-solvent comprising ethanol and water, and spray drying the dissolved antimicrobial agents with a spray dryer.

8. The process of claim 7, wherein the spray drying is performed with the following conditions:
5.5 μm spray mesh size;
0.65% (w/v) feed concentration;
2:1 ratio (v/v) water-ethanol co-solvent;
120 L/min nitrogen flow rate;
4 mL/h relative spray rate;
120° C. inlet temperature; and
60-65° C. outlet temperature.

9. The process of claim 3, wherein the dry powder inhaler composition is prepared by dissolving the antimicrobial agents in a co-solvent comprising ethanol and water, and spray drying the dissolved antimicrobial agents with a spray dryer.

10. The process of claim 9, wherein the spray drying is performed with the following conditions:
5.5 μm spray mesh size;
0.65% (w/v) feed concentration;
2:1 ratio (v/v) water-ethanol co-solvent;
120 L/min nitrogen flow rate;
4 mL/h relative spray rate;
120° C. inlet temperature; and
60-65° C. outlet temperature.

11. The process of claim 5, wherein the dry powder inhaler composition is prepared by dissolving the antimicrobial agents in a co-solvent comprising ethanol and water, and spray drying the dissolved antimicrobial agents with a spray dryer.

12. The process of claim 11, wherein the spray drying is performed with the following conditions:
5.5 μm spray mesh size;
0.65% (w/v) feed concentration;
2:1 ratio (v/v) water-ethanol co-solvent;
120 L/min nitrogen flow rate;
4 mL/h relative spray rate;
120° C. inlet temperature; and
60-65° C. outlet temperature.

13. The process of claim 1, wherein the tetracycline antibiotic is tigecycline, the polymyxin is colistin, the ansamycin is rifampicin and the carbapenem is meropenem.

14. The process of claim 3, wherein the tetracycline antibiotic is tigecycline, the polymyxin is colistin, the ansamycin is rifampicin and the carbapenem is meropenem.

15. The process of claim 5, wherein the tetracycline antibiotic is tigecycline, the polymyxin is colistin, the ansamycin is rifampicin and the carbapenem is meropenem.

16. The process of claim 1, wherein the dry powder inhaler composition comprises: colistin, tigecycline and rifampicin in a weight ratio of 5:4:12; or colistin, meropenem and tigecycline in a weight ratio of 5:4:4.

17. The process of claim 3, wherein the dry powder inhaler composition comprises: colistin, tigecycline and rifampicin in a weight ratio of 5:4:12; or colistin, meropenem and tigecycline in a weight ratio of 5:4:4.

18. The process of claim 5, wherein the dry powder inhaler composition comprises: colistin, tigecycline and rifampicin in a weight ratio of 5:4:12; or colistin, meropenem and tigecycline in a weight ratio of 5:4:4.

19. The process of claim 1, wherein the dry powder inhaler composition has a fine particle fraction of at least 50%.

20. The process of claim 3, wherein the dry powder inhaler composition has a fine particle fraction of at least 50%.

21. The process of claim 5, wherein the dry powder inhaler composition has a fine particle fraction of at least 50%.

* * * * *